United States Patent
Zewge et al.

(10) Patent No.: US 9,441,228 B2
(45) Date of Patent: Sep. 13, 2016

(54) POST-SYNTHETIC CHEMICAL MODIFICATION OF RNA AT THE 2'-POSITION OF THE RIBOSE RING VIA "CLICK" CHEMISTRY

(71) Applicant: SIRNA THERAPEUTICS, INC., Cambridge, MA (US)

(72) Inventors: Daniel Zewge, West Orange, NJ (US); Francis Gosselin, San Mateo, CA (US)

(73) Assignee: Sirna Therapeutics, Inc., Cambridge, MA (US)

( * ) Notice: Subject to any disclaimer, the term of this patent is extended or adjusted under 35 U.S.C. 154(b) by 0 days.

(21) Appl. No.: 14/609,118

(22) Filed: Jan. 29, 2015

(65) Prior Publication Data

US 2015/0211008 A1    Jul. 30, 2015

Related U.S. Application Data

(63) Continuation of application No. 13/574,136, filed as application No. PCT/US2011/021629 on Jan. 19, 2011, now abandoned.

(60) Provisional application No. 61/297,377, filed on Jan. 22, 2010, provisional application No. 61/325,908, filed on Apr. 20, 2010.

(51) Int. Cl.

| C07H 21/00 | (2006.01) |
|---|---|
| C12N 15/113 | (2010.01) |
| C07C 217/40 | (2006.01) |
| C07C 217/52 | (2006.01) |
| C07D 207/08 | (2006.01) |
| C07D 207/12 | (2006.01) |
| C07D 209/48 | (2006.01) |
| C07D 211/22 | (2006.01) |
| C07D 211/44 | (2006.01) |
| C07D 211/46 | (2006.01) |
| C07D 295/088 | (2006.01) |
| C07H 21/02 | (2006.01) |

(52) U.S. Cl.
CPC ........... *C12N 15/113* (2013.01); *C07C 217/40* (2013.01); *C07C 217/52* (2013.01); *C07D 207/08* (2013.01); *C07D 207/12* (2013.01); *C07D 209/48* (2013.01); *C07D 211/22* (2013.01); *C07D 211/44* (2013.01); *C07D 211/46* (2013.01); *C07D 295/088* (2013.01); *C07H 21/02* (2013.01); *C07C 2101/02* (2013.01); *C12N 2310/14* (2013.01); *C12N 2310/141* (2013.01); *C12N 2310/321* (2013.01)

(58) Field of Classification Search
CPC ............. C07C 217/40; C07C 217/52; C07C 2101/02; C07D 207/08; C07D 207/12; C07D 207/48; C07D 211/22; C07D 211/44; C07D 211/46; C07D 295/088; C07H 21/02; C12N 15/113; C12N 2310/321; C12N 2310/14; C12N 2310/141
See application file for complete search history.

(56) References Cited

U.S. PATENT DOCUMENTS

| 7,919,591 | B2 * | 4/2011 | Sheffer | ................ | C07K 14/765 435/320.1 |
|---|---|---|---|---|---|
| 8,022,186 | B2 * | 9/2011 | Sheffer | ................ | C07K 14/765 435/320.1 |
| 8,053,560 | B2 * | 11/2011 | Sheffer | ................ | C07K 14/765 435/320.1 |
| 8,114,636 | B2 * | 2/2012 | Agnew | ................ | C07D 207/40 422/422 |
| 8,618,257 | B2 * | 12/2013 | Sheffer | ................ | C07K 14/765 435/320.1 |
| 2008/0050731 | A1 | 2/2008 | Agnew et al. | | |

FOREIGN PATENT DOCUMENTS

WO    2010039548 A2    4/2010

OTHER PUBLICATIONS

Watts et al., "Chemically modified siRNA: tools and applications," Drug Discovery Today, 13(19-20): 842-855 (2008).
Berndl et al., "Comparision of a Nucleosidic vs Non-Nucleosidic Postsynthetic 'Click' Modification of DNA with Base-Labile Fluorescent Probes," Bioconjugate Chem., 20: 558-564 (2009).

* cited by examiner

*Primary Examiner* — Lawrence E Crane

(74) *Attorney, Agent, or Firm* — Jeffrey N. Townes; LeClairRyan

(57) ABSTRACT

This invention relates to a 2'-modified RNA agent comprising at least one RNA strand containing a 2'-O substituent having an alkyne functional group attaching to the O atom at the 2'-position on one or more ribose rings, wherein the 2'-O substituent is located at one or more of positions 2, 3, 4, 7, 8, 9, 10, 11, 13, 14, and 16, from 5'-end of the RNA strand. This invention also relates to a 2'-modified RNA agent comprising at least one RNA strand containing a 2'-O substituent having a triazole functional group attaching to the O atom at the 2'-position on one or more ribose rings, wherein the 2'-O substituent is located at one or more of positions 2, 3, 4, 7, 8, 9, 10, 11, 13, 14, and 16, from 5'-end of the RNA strand.

18 Claims, 9 Drawing Sheets

US 9,441,228 B2

POST-SYNTHETIC CHEMICAL MODIFICATION OF RNA AT THE 2'-POSITION OF THE RIBOSE RING VIA "CLICK" CHEMISTRY

CROSS-REFERENCE TO RELATED APPLICATIONS

This application is a continuation application of U.S. patent application Ser. No. 13/574,136, filed Jul. 19, 2012, which is a national stage application of PCT Application No. PCT/US2011/021629, filed Jan. 19, 2011, which claims the benefit of priority to U.S. Provisional Patent Application No. 61/297,377, filed Jan. 22, 2010, and U.S. Provisional Application No. 61/325,908, filed Apr. 20, 2010; all of which are incorporated by reference herein in their entirety.

BACKGROUND OF THE INVENTION

RNA interference (RNAi) is an evolutionarily conserved cellular mechanism of post-transcriptional gene silencing found in fungi, plants and animals that uses small RNA molecules to inhibit gene expression in a sequence-specific manner. The RNAi machinery can be harnessed to destruct any mRNA of a known sequence. This allows for suppression (knock-down) of any gene from which it was generated and consequently preventing the synthesis of the target protein. Smaller siRNA duplexes introduced exogenously were found to be equally effective triggers of RNAi (Zamore, P. D., Tuschl, T., Sharp, P. A., Bartel, D. P. *Cell* 2000, 101, 25-33). Synthetic RNA duplexes can be used to modulate therapeutically relevant biochemical pathways, including ones which are not accessible through traditional small molecule control.

Chemical modification of RNA leads to improved physical and biological properties such as nuclease stability (Damha et al *Drug Discovery Today* 2008, 13(19/20), 842-855), reduced immune stimulation (Sioud *TRENDS in Molecular Medicine* 2006, 12(4), 167-176), enhanced binding (Koller, E. et al *Nucl. Acids Res.* 2006, 34, 4467-4476), enhanced lipophilic character to improve cellular uptake and delivery to the cytoplasm.

Chemical modifications of RNA have relied heavily on work-intensive, cumbersome, multi-step syntheses of structurally novel nucleoside analogues and their corresponding phosphoramidites prior to RNA assembly. In particular, a major emphasis has been placed on chemical modification of the 2'-position of nucleosides. A rigorous approach to structure-activity-relationship (SAR) studies of chemical modifications will obviously require synthesis and evaluation of all four canonical ribonucleosides [adenosine (A), cytidine (C), uridine (U), guanosine (G)]. Furthermore, some chemical modifications bear sensitive functional groups that may be incompatible with state-of-the-art automated synthesis of RNA as well as subsequent downstream cleavage-deprotection steps. These attributes have made chemical modification of RNA prior to synthesis rather low-throughput and limited in scope.

Post-synthetic chemical modifications of RNA have centered for the most part on simple conjugation chemistry. Conjugation has largely been performed on either the 3' or the 5'-end of the RNA via alkylamine and disulfide linkers. These modifications have allowed conjugation of RNA to various compounds such as cholesterol, fatty acids, poly (ethylene)glycols, various delivery vehicles and targeting agents such as poly(amines), peptides, peptidomimetics, and carbohydrates.

This invention relates to the post-synthetic chemical modification of RNA at the 2'-postion on the ribose ring via a copper catalyzed Huisgen cycloaddition ("click" chemistry: Kolb, Sharpless *Drug Discovery Today* 2003, 8, 1128). The invention 1) avoids complex, tedious multi-step syntheses of each desired modified ribonucleoside; 2) allows diverse chemical modifications using high-fidelity chemistry that is completely orthogonal to commonly used alkylamino, carboxylate and disulfide linker reactivities; 3) allows introduction of functional groups that are incompatible with modern automated solid-phase synthesis of RNA and subsequent cleavage-deprotection steps; 4) allows introduction of functional groups useful as targeting ligands; and 5) enables high-throughput structure-activity relationship studies on chemically modified RNA in 96-well format.

SUMMARY OF THE INVENTION

Figure 1:
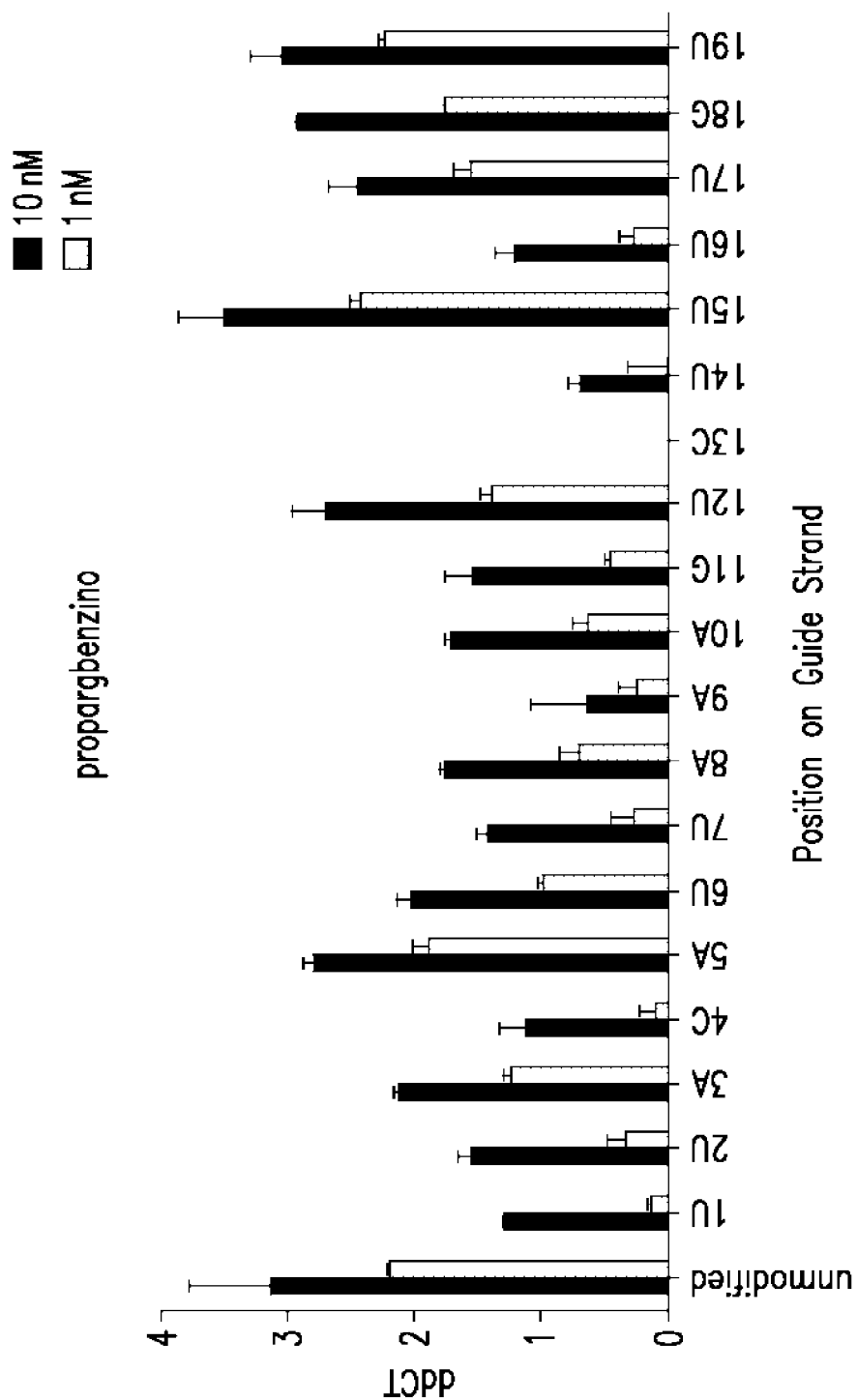
FIG. 1. Systematic evaluation of the impact on knockdown of the 2'-O-benzyl-triazole inosine chemical modification along positions 1 through 19 of the guide strand of a SSB(291) siRNA.

This invention relates to the post-synthetic chemical modification of RNA at the 2'-position on the ribose ring via a copper catalyzed Huisgen cycloaddition ("click" chemistry: Kolb, Sharpless *Drug Discovery Today* 2003, 8, 1128). The invention 1) avoids complex, tedious multi-step syntheses of each desired modified ribonucleoside; 2) allows diverse chemical modifications using high-fidelity chemistry that is completely orthogonal to commonly used alkylamino, carboxylate and disulfide linker reactivities; 3) allows introduction of functional groups that are incompatible with modern automated solid-phase synthesis of RNA and subsequent cleavage-deprotection steps; 4) allows introduction of functional groups useful as targeting ligands; and 5) enables high-throughput structure-activity relationship studies on chemically modified RNA in 96-well format.

DETAILED DESCRIPTION OF THE INVENTION

Methods for the synthesis of nucleotide derivatives wherein molecules of interest are grafted on the oligonucleotide with the help of a "click chemistry" reaction between an azide function on the molecule of interest and an alkyne function on the oligonucleotide are demonstrated in US 2009/0124571. This work discloses molecules such as carbohydrates, peptides, lipids, oligonucleotides, biotin, ferrocenyl compounds and fluorescent tags which are grafted onto oligonucleotides utilizing alkyne phosphoester derivatives of the oligonucleotides to make the 1,3-cycloaddition with an azide-substituted molecule of interest.

Methods for forming azido-modified nucleic acid conjugates of reporter molecules, carrier molecules or solid support utilizing "click chemistry" are disclosed in US 2008/0050731.

Thus the prior art discloses the use of "click chemistry" to generate modified oligonucleotides wherein the alkyne functional group is on the phosphate backbone or the base in DNA and RNA molecules or the alkyne functional group is on the ribose of DNA molecules. Typically, the modification is for labeling purposes.

The use of "click chemistry" to generate 2'-modified RNA wherein the alkyne functional group is on the ribose is not known. There are considerable differences in the physico-chemical properties of RNA and DNA. For example, it is well recognized that RNA is much less stable than DNA towards hydrolysis. Furthermore, RNA can undergo auto-catalytic cleavage via intramolecular cyclization of the 2'-position onto the 3'-phosphodiester. Modification of the 2'-position is critical for RNA stability and therapeutic applicability.

RNA with alkyne functional group at the 2'-position.

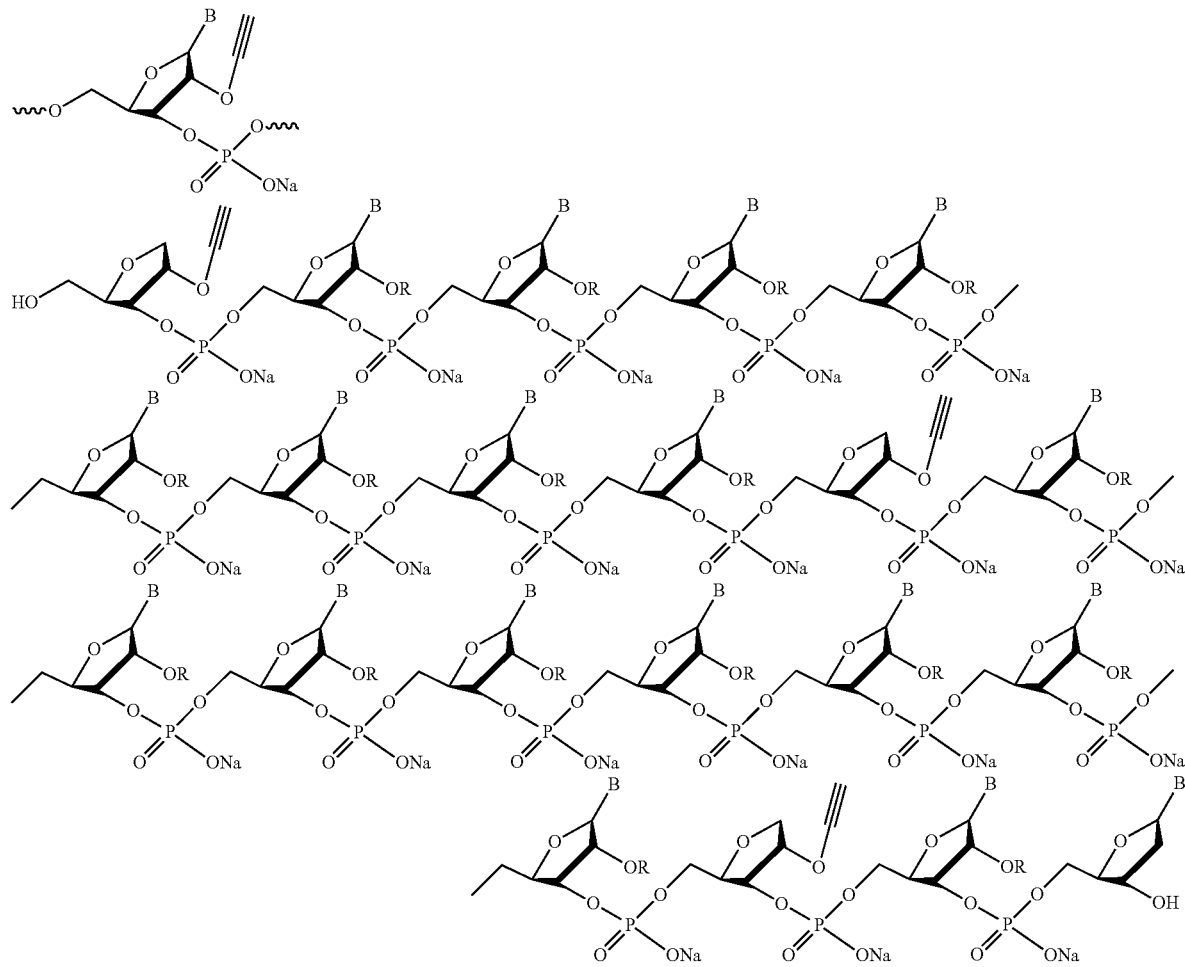

R = H, TBS

Synthesis of modified RNA and DNA utilizing an alkyne handle on a base and subsequent "click chemistry" is disclosed in WO 2008/052775 and in CN 101550175.

Recent reviews regarding "click chemistry" and oligonucleotide synthesis are covered by Gramlich et al. *Angew. Chem. Int. Ed.* 2008, 47, 8350-8358; Amblard et al. *Chem. Rev.* 2009, 109, 4207-4220.

The current invention relates to chemical modification of RNA at the 2'-position of the ribose ring based on the 1,3-dipolar cycloaddition (Huisgen reaction) between alkynes and azides. The 1,3-dipolar cycloaddition (Huisgen reaction) between alkynes and azides is known. (Tornøe, Christensen, Meldal *J. Org. Chem.* 2002, 67, 3057;

Rostovstev, Green, Fokin, Sharpless *Angew. Chem. Int. Ed.* 2002, 41, 2596).

In an embodiment, the invention provides a process for introducing 2'-modifications into RNA, said process comprises a) obtaining RNA with an alkyne functional group at the 2'-position on at least one ribose ring; b) creating a solution of RNA in a solvent; and c) adding an organic azide and a metal catalyst to the solution to form a reaction and creating a 2'-modified RNA.

In an embodiment, the process is conducted in high-throughput format.

In an embodiment, the step (a) RNA may be purchased or synthesized.

In an embodiment, the step (b) solvent is selected from aqueous buffer solutions (including phosphate buffers), aqueous DMSO, CH$_3$CN, DMF, DMAc, NMP and a suitable ionic liquid.

In an embodiment, the step (b) solvent is aqueous DMSO.

In an embodiment, the step (c) metal catalyst is selected from copper and ruthenium.

In an embodiment, the step (c) metal catalyst is copper.

In an embodiment, the step (c) metal catalyst is copper with a suitable ligand to stabilize the Cu(I) oxidation state.

In an embodiment, the step (c) reaction is performed at temperatures between −20-300° C. for 0 to 18 h.

In an embodiment, the step (c) reaction is performed at temperatures between 5-120° C. for 0.5 to 18 h.

In an embodiment, the step (c) reaction is performed at temperatures between 20-100° C. for 0.5 to 18 h.

In an embodiment, the step (c) reaction is performed at temperatures between 60-90° C. for 0.5 to 18 h.

In an embodiment, the step (c) reaction is performed at temperatures between 65-80° C. for 0.5 to 18 h.

In another embodiment, the invention provides a process for introducing 2'-modifications into RNA, said process comprises a) obtaining RNA with an alkyne functional group at the 2'-position on at least one ribose ring of an internal nucleotide; b) creating a solution of RNA in a solvent; and c) adding an organic azide and a metal catalyst to the solution to form a reaction and creating a 2'-modified RNA.

In an embodiment, the process is conducted in high-throughput format.

In an embodiment, the step (a) RNA may be purchased or synthesized.

In an embodiment, the step (b) solvent is selected from aqueous buffer solutions (including phosphate buffers), aqueous DMSO, CH$_3$CN, DMF, DMAc, NMP and a suitable ionic liquid.

In an embodiment, the step (b) solvent is aqueous DMSO.

In an embodiment, the step (c) metal catalyst is selected from copper and ruthenium.

In an embodiment, the step (c) metal catalyst is copper.

In an embodiment, the step (c) metal catalyst is copper with a suitable ligand to stabilize the Cu(I) oxidation state.

In an embodiment, the step (c) reaction is performed at temperatures between −20-300° C. for 0 to 18 h.

In an embodiment, the step (c) reaction is performed at temperatures between 5-120° C. for 0.5 to 18 h.

In an embodiment, the step (c) reaction is performed at temperatures between 20-100° C. for 0.5 to 18 h.

In an embodiment, the step (c) reaction is performed at temperatures between 60-90° C. for 0.5 to 18 h.

In an embodiment, the step (c) reaction is performed at temperatures between 65-80° C. for 0.5 to 18 h.

In another embodiment, the invention provides a process for introducing 2'-modifications into RNA, said process comprises a) obtaining RNA with an alkyne functional group at the 2'-position on at least one ribose ring of an internal nucleotide; b) creating a solution of RNA in a solvent; c) adding an organic azide and a metal catalyst to the solution to form a reaction and creating a 2'-modified RNA; and d) purifying the 2'-modified RNA.

In an embodiment, the step (a) RNA may be purchased or synthesized.

In an embodiment, the step (c) solvent is selected from aqueous buffer solutions (including phosphate buffers), aqueous DMSO, CH$_3$CN, DMF, DMAc, NMP and a suitable ionic liquid.

In an embodiment, the step (c) solvent is aqueous DMSO.

In an embodiment, the step (c) metal catalyst is selected from copper and ruthenium.

In an embodiment, the step (c) metal catalyst is copper.

In an embodiment, the step (c) metal catalyst is copper with a suitable ligand to stabilize Cu(I) oxidation state.

In an embodiment, the step (c) reaction is performed at temperatures between −20-300° C. for 0 to 18 h.

In an embodiment, the step (c) reaction is performed at temperatures between 5-120° C. for 0.5 to 18 h.

In an embodiment, the step (c) reaction is performed at temperatures between 20-100° C. for 0.5 to 18 h.

In an embodiment, the step (c) reaction is performed at temperatures between 60-90° C. for 0.5 to 18 h.

In an embodiment, the step (c) reaction is performed at temperatures between 65-80° C. for 0.5 to 18 h.

In an embodiment, the step (d) purification is performed in high-throughput format on 96-well C18 cartridges (solid-phase extraction) or strong-anion-exchange-HPLC or reverse-phase HPLC or poly(acrylamide) gel electrophoresis (PAGE) or size-exclusion chromatography.

In another embodiment, the invention provides a process for introducing 2'-modifications into RNA, said process comprises a) obtaining RNA with an alkyne functional group at the 2'-position on at least one ribose ring of an internal nucleotide; b) creating a solution of RNA in a solvent; c) adding an organic azide and a metal catalyst to the solution to form a reaction and creating a 2'-modified RNA; d) cooling the solution and adding a fluoride source; e) heating the solution; f) cooling the solution and adding a diluent; and g) purifying the 2'-modified RNA.

In an embodiment, the step (a) RNA may be purchased or synthesized.

In an embodiment, the step (c) solvent is selected from aqueous buffer solutions (including phosphate buffers), aqueous DMSO, CH$_3$CN, DMF, DMAc, NMP and a suitable ionic liquid.

In an embodiment, the step (c) solvent is aqueous DMSO.

In an embodiment, the step (c) metal catalyst is selected from copper and ruthenium.

In an embodiment, the step (c) metal catalyst is copper.

In an embodiment, the step (c) metal catalyst is copper with a suitable ligand to stabilize Cu(I) oxidation state.

In an embodiment, the step (c) reaction is performed at temperatures between −20-300° C. for 0 to 18 h.

In an embodiment, the step (c) reaction is performed at temperatures between 5-120° C. for 0.5 to 18 h.

In an embodiment, the step (c) reaction is performed at temperatures between 20-100° C. for 0.5 to 18 h.

In an embodiment, the step (c) reaction is performed at temperatures between 60-90° C. for 0.5 to 18 h.

In an embodiment, the step (c) reaction is performed at temperatures between 65-80° C. for 0.5 to 18 h.

In an embodiment, the step (e) fluoride source is Et₃N.3HF, tetrabutylammonium fluoride, potassium fluoride and ammonium fluoride.

In an embodiment, the step (e) fluoride source is ammonium fluoride.

In an embodiment, the step (f) diluent is NaCl.

In an embodiment, the step (g) purification is performed in high-throughput format on 96-well C18 cartridges (solid-phase extraction) or strong-anion-exchange-HPLC or reverse-phase HPLC or poly(acrylamide) gel electrophoresis (PAGE) or size-exclusion chromatography.

In another embodiment, the instant invention also discloses a method for attaching targeting ligands to RNA utilizing the process described herein.

In another embodiment, the instant invention further discloses a method for attaching targeting ligands to internal nucleotides in RNA utilizing the process described herein.

In an embodiment, the invention provides a RNA with an alkyne functional group at the 2'-position on one or more ribose rings.

In another embodiment, the invention provides a RNA with an alkyne functional group at the 2'-position on two or more ribose rings.

In another embodiment, the invention provides a RNA with an alkyne functional group at the 2'-position on three or more ribose rings.

In another embodiment, the invention provides a RNA with an alkyne functional group at the 2'-position on four or more ribose rings.

In another embodiment, the invention provides a RNA with an alkyne functional group at the 2'-position on five or more ribose rings.

In another embodiment, the invention provides a RNA with an alkyne functional group at the 2'-position on six or more ribose rings.

In another embodiment, the invention provides a RNA with an alkyne functional group at the 2'-position on seven or more ribose rings.

In another embodiment, the invention provides a RNA with an alkyne functional group at the 2'-position on eight or more ribose rings.

In another embodiment, the invention provides a RNA with an alkyne functional group at the 2'-position on nine or more ribose rings.

In another embodiment, the invention provides a RNA with an alkyne functional group at the 2'-position on ten or more ribose rings.

In an embodiment, the invention provides a RNA with an alkyne functional group at the 2'-position on one or more ribose rings excluding the external 5' and 3' ribose rings.

In another embodiment, the invention provides a RNA with an alkyne functional group at the 2'-position on two or more ribose rings excluding the external 5' and 3' ribose rings.

In another embodiment, the invention provides a RNA with an alkyne functional group at the 2'-position on three or more ribose rings excluding the external 5' and 3' ribose rings.

In another embodiment, the invention provides a RNA with an alkyne functional group at the 2'-position on four or more ribose rings excluding the external 5' and 3' ribose rings.

In another embodiment, the invention provides a RNA with an alkyne functional group at the 2'-position on five or more ribose rings excluding the external 5' and 3' ribose rings.

In another embodiment, the invention provides a RNA with an alkyne functional group at the 2'-position on six or more ribose rings excluding the external 5' and 3' ribose rings.

In another embodiment, the invention provides a RNA with an alkyne functional group at the 2'-position on seven or more ribose rings excluding the external 5' and 3' ribose rings.

In another embodiment, the invention provides a RNA with an alkyne functional group at the 2'-position on eight or more ribose rings excluding the external 5' and 3' ribose rings.

In another embodiment, the invention provides a RNA with an alkyne functional group at the 2'-position on nine or more ribose rings excluding the external 5' and 3' ribose rings.

In another embodiment, the invention provides a RNA with an alkyne functional group at the 2'-position on ten or more ribose rings excluding the external 5' and 3' ribose rings.

In an embodiment, the invention provides a miRNA with an alkyne functional group at the 2'-position on one or more ribose rings.

In another embodiment, the invention provides a miRNA with an alkyne functional group at the 2'-position on two or more ribose rings.

In another embodiment, the invention provides a miRNA with an alkyne functional group at the 2'-position on three or more ribose rings.

In another embodiment, the invention provides a miRNA with an alkyne functional group at the 2'-position on four or more ribose rings.

In another embodiment, the invention provides a miRNA with an alkyne functional group at the 2'-position on five or more ribose rings.

In another embodiment, the invention provides a miRNA with an alkyne functional group at the 2'-position on six or more ribose rings.

In another embodiment, the invention provides a miRNA with an alkyne functional group at the 2'-position on seven or more ribose rings.

In another embodiment, the invention provides a miRNA with an alkyne functional group at the 2'-position on eight or more ribose rings.

In another embodiment, the invention provides a miRNA with an alkyne functional group at the 2'-position on nine or more ribose rings.

In another embodiment, the invention provides a miRNA with an alkyne functional group at the 2'-position on ten or more ribose rings.

In an embodiment, the invention provides a miRNA with an alkyne functional group at the 2'-position on one or more ribose rings excluding the external 5' and 3' ribose rings.

In another embodiment, the invention provides a miRNA with an alkyne functional group at the 2'-position on two or more ribose rings excluding the external 5' and 3' ribose rings.

In another embodiment, the invention provides a miRNA with an alkyne functional group at the 2'-position on three or more ribose rings excluding the external 5' and 3' ribose rings.

In another embodiment, the invention provides a miRNA with an alkyne functional group at the 2'-position on four or more ribose rings excluding the external 5' and 3' ribose rings.

In another embodiment, the invention provides a miRNA with an alkyne functional group at the 2'-position on five or more ribose rings excluding the external 5' and 3' ribose rings.

In another embodiment, the invention provides a miRNA with an alkyne functional group at the 2'-position on six or more ribose rings excluding the external 5' and 3' ribose rings.

In another embodiment, the invention provides a miRNA with an alkyne functional group at the 2'-position on seven or more ribose rings excluding the external 5' and 3' ribose rings.

In another embodiment, the invention provides a miRNA with an alkyne functional group at the 2'-position on eight or more ribose rings excluding the external 5' and 3' ribose rings.

In another embodiment, the invention provides a miRNA with an alkyne functional group at the 2'-position on nine or more ribose rings excluding the external 5' and 3' ribose rings.

In another embodiment, the invention provides a miRNA with an alkyne functional group at the 2'-position on ten or more ribose rings excluding the external 5' and 3' ribose rings.

In an embodiment, the invention provides a siRNA with an alkyne functional group at the 2'-position on one or more ribose rings.

In another embodiment, the invention provides a siRNA with an alkyne functional group at the 2'-position on two or more ribose rings.

In another embodiment, the invention provides a siRNA with an alkyne functional group at the 2'-position on three or more ribose rings.

In another embodiment, the invention provides a siRNA with an alkyne functional group at the 2'-position on four or more ribose rings.

In another embodiment, the invention provides a siRNA with an alkyne functional group at the 2'-position on five or more ribose rings.

In another embodiment, the invention provides a siRNA with an alkyne functional group at the 2'-position on six or more ribose rings.

In another embodiment, the invention provides a siRNA with an alkyne functional group at the 2'-position on seven or more ribose rings.

In another embodiment, the invention provides a siRNA with an alkyne functional group at the 2'-position on eight or more ribose rings.

In another embodiment, the invention provides a siRNA with an alkyne functional group at the 2'-position on nine or more ribose rings.

In another embodiment, the invention provides a siRNA with an alkyne functional group at the 2'-position on ten or more ribose rings.

In an embodiment, the invention provides a siRNA with an alkyne functional group at the 2'-position on one or more ribose rings excluding the external 5' and 3' ribose rings.

In another embodiment, the invention provides a siRNA with an alkyne functional group at the 2'-position on two or more ribose rings excluding the external 5' and 3' ribose rings.

In another embodiment, the invention provides a siRNA with an alkyne functional group at the 2'-position on three or more ribose rings excluding the external 5' and 3' ribose rings.

In another embodiment, the invention provides a siRNA with an alkyne functional group at the 2'-position on four or more ribose rings excluding the external 5' and 3' ribose rings.

In another embodiment, the invention provides a siRNA with an alkyne functional group at the 2'-position on five or more ribose rings excluding the external 5' and 3' ribose rings.

In another embodiment, the invention provides a siRNA with an alkyne functional group at the 2'-position on six or more ribose rings excluding the external 5' and 3' ribose rings.

In another embodiment, the invention provides a siRNA with an alkyne functional group at the 2'-position on seven or more ribose rings excluding the external 5' and 3' ribose rings.

In another embodiment, the invention provides a siRNA with an alkyne functional group at the 2'-position on eight or more ribose rings excluding the external 5' and 3' ribose rings.

In another embodiment, the invention provides a siRNA with an alkyne functional group at the 2'-position on nine or more ribose rings excluding the external 5' and 3' ribose rings.

In another embodiment, the invention provides a siRNA with an alkyne functional group at the 2'-position on ten or more ribose rings excluding the external 5' and 3' ribose rings.

In an embodiment, the invention provides a siRNA with an alkyne functional group at the 2'-position on one ribose ring.

In another embodiment, the invention provides a siRNA with an alkyne functional group at the 2'-position on two ribose rings.

In another embodiment, the invention provides a siRNA with an alkyne functional group at the 2'-position on three ribose rings.

In another embodiment, the invention provides a siRNA with an alkyne functional group at the 2'-position on four ribose rings.

In another embodiment, the invention provides a siRNA with an alkyne functional group at the 2'-position on five ribose rings.

In another embodiment, the invention provides a siRNA with an alkyne functional group at the 2'-position on six ribose rings.

In another embodiment, the invention provides a siRNA with an alkyne functional group at the 2'-position on seven ribose rings.

In another embodiment, the invention provides a siRNA with an alkyne functional group at the 2'-position on eight ribose rings.

In another embodiment, the invention provides a siRNA with an alkyne functional group at the 2'-position on nine ribose rings.

In another embodiment, the invention provides a siRNA with an alkyne functional group at the 2'-position on ten ribose rings.

In an embodiment, the invention provides a siRNA with an alkyne functional group at the 2'-position on one ribose ring excluding the external 5' and 3' ribose rings.

In another embodiment, the invention provides a siRNA with an alkyne functional group at the 2'-position on two ribose rings excluding the external 5' and 3' ribose rings.

In another embodiment, the invention provides a siRNA with an alkyne functional group at the 2'-position on three ribose rings excluding the external 5' and 3' ribose rings.

In another embodiment, the invention provides a siRNA with an alkyne functional group at the 2'-position on four ribose rings excluding the external 5' and 3' ribose rings.

In another embodiment, the invention provides a siRNA with an alkyne functional group at the 2'-position on five ribose rings excluding the external 5' and 3' ribose rings.

In another embodiment, the invention provides a siRNA with an alkyne functional group at the 2'-position on six ribose rings excluding the external 5' and 3' ribose rings.

In another embodiment, the invention provides a siRNA with an alkyne functional group at the 2'-position on seven ribose rings excluding the external 5' and 3' ribose rings.

In another embodiment, the invention provides a siRNA with an alkyne functional group at the 2'-position on eight ribose rings excluding the external 5' and 3' ribose rings.

In another embodiment, the invention provides a siRNA with an alkyne functional group at the 2'-position on nine ribose rings excluding the external 5' and 3' ribose rings.

In another embodiment, the invention provides a siRNA with an alkyne functional group at the 2'-position on ten ribose rings excluding the external 5' and 3' ribose rings.

In an embodiment, the invention provides the guide strand of the siRNA with an alkyne functional group at the 2'-position on one ribose ring.

In another embodiment, the invention provides the guide strand of the siRNA with an alkyne functional group at the 2'-position on two ribose rings.

In another embodiment, the invention provides the guide strand of the siRNA with an alkyne functional group at the 2'-position on three ribose rings.

In another embodiment, the invention provides the guide strand of the siRNA with an alkyne functional group at the 2'-position on four ribose rings.

In another embodiment, the invention provides the guide strand of the siRNA with an alkyne functional group at the 2'-position on five ribose rings.

In another embodiment, the invention provides the guide strand of the siRNA with an alkyne functional group at the 2'-position on six ribose rings.

In another embodiment, the invention provides the guide strand of the siRNA with an alkyne functional group at the 2'-position on seven ribose rings.

In another embodiment, the invention provides the guide strand of the siRNA with an alkyne functional group at the 2'-position on eight ribose rings.

In another embodiment, the invention provides the guide strand of the siRNA with an alkyne functional group at the 2'-position on nine ribose rings.

In another embodiment, the invention provides the guide strand of the siRNA with an alkyne functional group at the 2'-position on ten ribose rings.

In an embodiment, the invention provides the guide strand of the siRNA with an alkyne functional group at the 2'-position on one ribose ring excluding the external 5' and 3' ribose rings.

In another embodiment, the invention provides the guide strand of the siRNA with an alkyne functional group at the 2'-position on two ribose rings excluding the external 5' and 3' ribose rings.

In another embodiment, the invention provides the guide strand of the siRNA with an alkyne functional group at the 2'-position on three ribose rings excluding the external 5' and 3' ribose rings.

In another embodiment, the invention provides the guide strand of the siRNA with an alkyne functional group at the 2'-position on four ribose rings excluding the external 5' and 3' ribose rings.

In another embodiment, the invention provides the guide strand of the siRNA with an alkyne functional group at the 2'-position on five ribose rings excluding the external 5' and 3' ribose rings.

In another embodiment, the invention provides the guide strand of the siRNA with an alkyne functional group at the 2'-position on six ribose rings excluding the external 5' and 3' ribose rings.

In another embodiment, the invention provides the guide strand of the siRNA with an alkyne functional group at the 2'-position on seven ribose rings excluding the external 5' and 3' ribose rings.

In another embodiment, the invention provides the guide strand of the siRNA with an alkyne functional group at the 2'-position on eight ribose rings excluding the external 5' and 3' ribose rings.

In another embodiment, the invention provides the guide strand of the siRNA with an alkyne functional group at the 2'-position on nine ribose rings excluding the external 5' and 3' ribose rings.

In another embodiment, the invention provides the guide strand of the siRNA with an alkyne functional group at the 2'-position on ten ribose rings excluding the external 5' and 3' ribose rings.

In an embodiment, the invention provides the passenger strand of the siRNA with an alkyne functional group at the 2'-position on one ribose ring.

In another embodiment, the invention provides the passenger strand of the siRNA with an alkyne functional group at the 2'-position on two ribose rings.

In another embodiment, the invention provides the passenger strand of the siRNA with an alkyne functional group at the 2'-position on three ribose rings.

In another embodiment, the invention provides the passenger strand of the siRNA with an alkyne functional group at the 2'-position on four ribose rings.

In another embodiment, the invention provides the passenger strand of the siRNA with an alkyne functional group at the 2'-position on five ribose rings.

In another embodiment, the invention provides the passenger strand of the siRNA with an alkyne functional group at the 2'-position on six ribose rings.

In another embodiment, the invention provides the passenger strand of the siRNA with an alkyne functional group at the 2'-position on seven ribose rings.

In another embodiment, the invention provides the passenger strand of the siRNA with an alkyne functional group at the 2'-position on eight ribose rings.

In another embodiment, the invention provides the passenger strand of the siRNA with an alkyne functional group at the 2'-position on nine ribose rings.

In another embodiment, the invention provides the passenger strand of the siRNA with an alkyne functional group at the 2'-position on ten ribose rings.

In an embodiment, the invention provides the passenger strand of the siRNA with an alkyne functional group at the 2'-position on one ribose ring excluding the external 5' and 3' ribose rings.

In another embodiment, the invention provides the passenger strand of the siRNA with an alkyne functional group at the 2'-position on two ribose rings excluding the external 5' and 3' ribose rings.

In another embodiment, the invention provides the passenger strand of the siRNA with an alkyne functional group at the 2'-position on three ribose rings excluding the external 5' and 3' ribose rings.

In another embodiment, the invention provides the passenger strand of the siRNA with an alkyne functional group at the 2'-position on four ribose rings excluding the external 5' and 3' ribose rings.

In another embodiment, the invention provides the passenger strand of the siRNA with an alkyne functional group at the 2'-position on five ribose rings excluding the external 5' and 3' ribose rings.

In another embodiment, the invention provides the passenger strand of the siRNA with an alkyne functional group at the 2'-position on six ribose rings excluding the external 5' and 3' ribose rings.

In another embodiment, the invention provides the passenger strand of the siRNA with an alkyne functional group at the 2'-position on seven ribose rings excluding the external 5' and 3' ribose rings.

In another embodiment, the invention provides the passenger strand of the siRNA with an alkyne functional group at the 2'-position on eight ribose rings excluding the external 5' and 3' ribose rings.

In another embodiment, the invention provides the passenger strand of the siRNA with an alkyne functional group at the 2'-position on nine ribose rings excluding the external 5' and 3' ribose rings.

In another embodiment, the invention provides the passenger strand of the siRNA with an alkyne functional group at the 2'-position on ten ribose rings excluding the external 5' and 3' ribose rings.

Definitions

"2'-modified RNA" means a RNA wherein at least one ribose ring is modified at the 2'-position.

"Alkyne functional group" means any chemical compound containing an alkyne functional group. The preferred "Alkyne functional group" is the propargyl moiety shown throughout this disclosure.

"High-throughput format" means that several operations are run in parallel fashion such as for example in 96-well plate chemical synthesis, 96-well plate purification, 96-well plate chromatographic analysis and 96-well plate mass spectrometric analysis.

"Internal nucleotide" means a nucleotide in an RNA molecule that is not at the 3'- or 5'-end. For example, the internal nucleotides in a 21mer siRNA occur at positions 2-20.

"RNA" means a chemically modified or unmodified ribonucleic acid molecule (single stranded or double stranded) comprising at least 3 nucleotides, including but not limited to miRNA and siRNA. In another embodiment, "RNA" means miRNA. In another embodiment, "RNA" means siRNA. Chemical modifications include, for example, modifications to the base, ribose ring (excluding modifications to the 2'-position), and phosphate backbone. The base can be a canonical base (A, G, T and U) or a modified or universal base (including but not limited to inosine and nitroindole).

"Organic azide" means any chemical compound containing the azide functional group.

"Metal catalyst" means any chemical form of copper and ruthenium, including solid-supported variants. Examples of metal catalyst include CuBr, CuBr.Me$_2$S, CuI, CuSO$_4$ or CuOAc and a suitable reducing agent such as sodium ascorbate, Cu(CH$_3$CN)$_4$PF$_6$, CpRuCl (PPh$_3$)$_2$, and Cp*RuCl (PPh$_3$)$_2$.

"Ribose ring" means the ribose moiety in a ribonucleotide.

"Targeting ligand" means a conjugate delivery moiety capable of delivering an oligonucleotide to a target cell of interest. Targeting ligands include, but are not limited to, lipids (cholesterol), sugars (NAG), proteins (transferrin), peptides, poly(ethylene)glycols and antibodies. See Juliano et al., *Nucleic Acids Research,* 2008, 1-14, doi:10.1093/nar/gkn342.

Utility

The present invention provides a process for introducing chemical modifications into RNA at the 2'-position on the ribose ring. It is well known in the art that RNA are useful for therapeutic and research purposes.

RNA Synthesis

The synthesis of RNA is well known in the art.

General Working Example "Click Reaction"

A suitable 2'-O-propargyl nucleoside phosphoramidite is incorporated into RNA using modern techniques based on the phosphoramidite approach. The crude, solid-support bound protected oligonucleotide is then treated with aqueous methylamine to remove nucleobase and phosphate protecting groups. The crude product is then lyophilized to remove volatiles. The crude product is dissolved in DMSO:H$_2$O, treated with a suitable organic azide and a copper catalyst. After aging an appropriate amount of time, the reaction mixture is treated with fluoride to remove the 2'-O-tert-butyldimethylsilyl protecting groups. The crude product is then purified to obtain the chemically modified RNA.

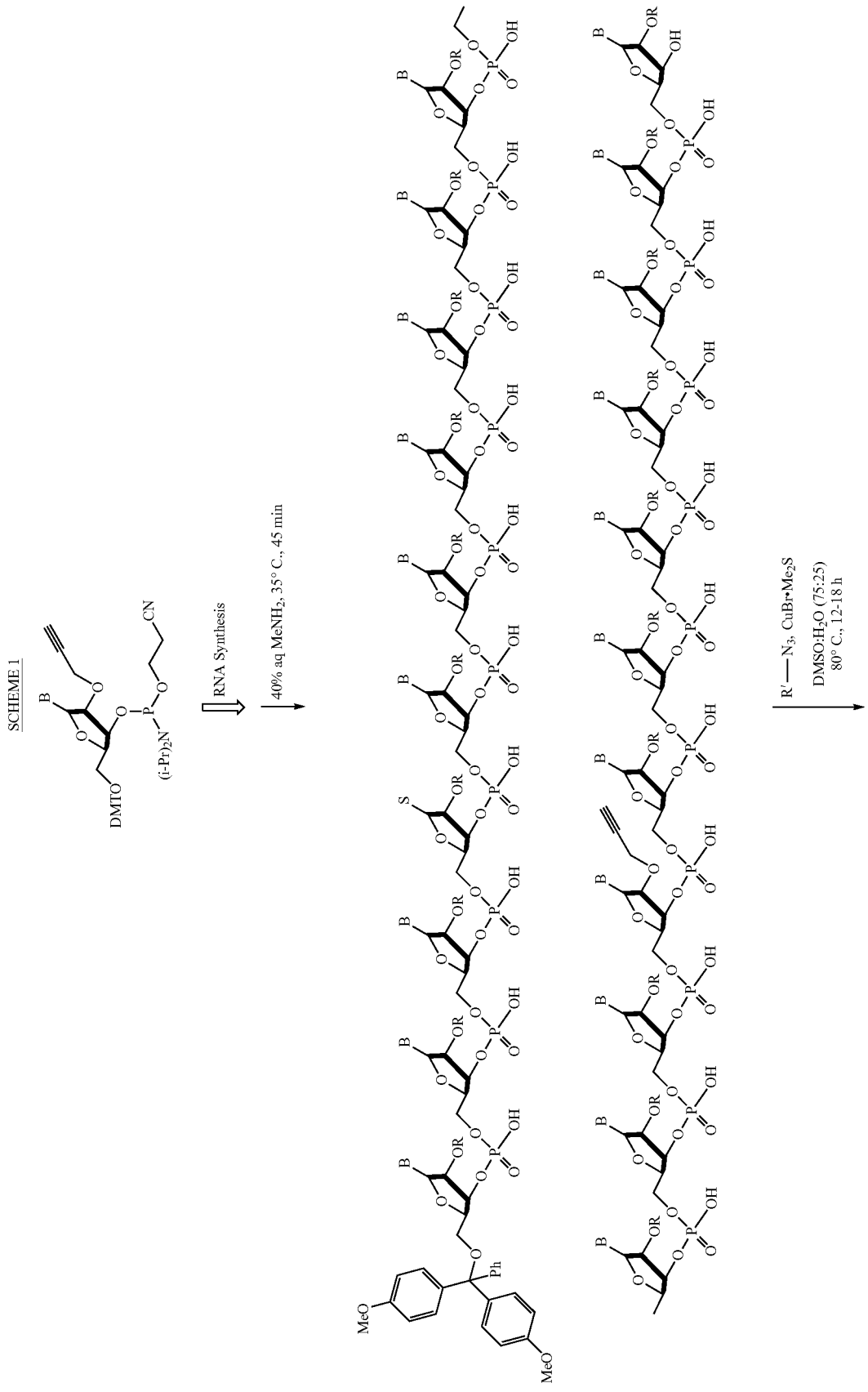

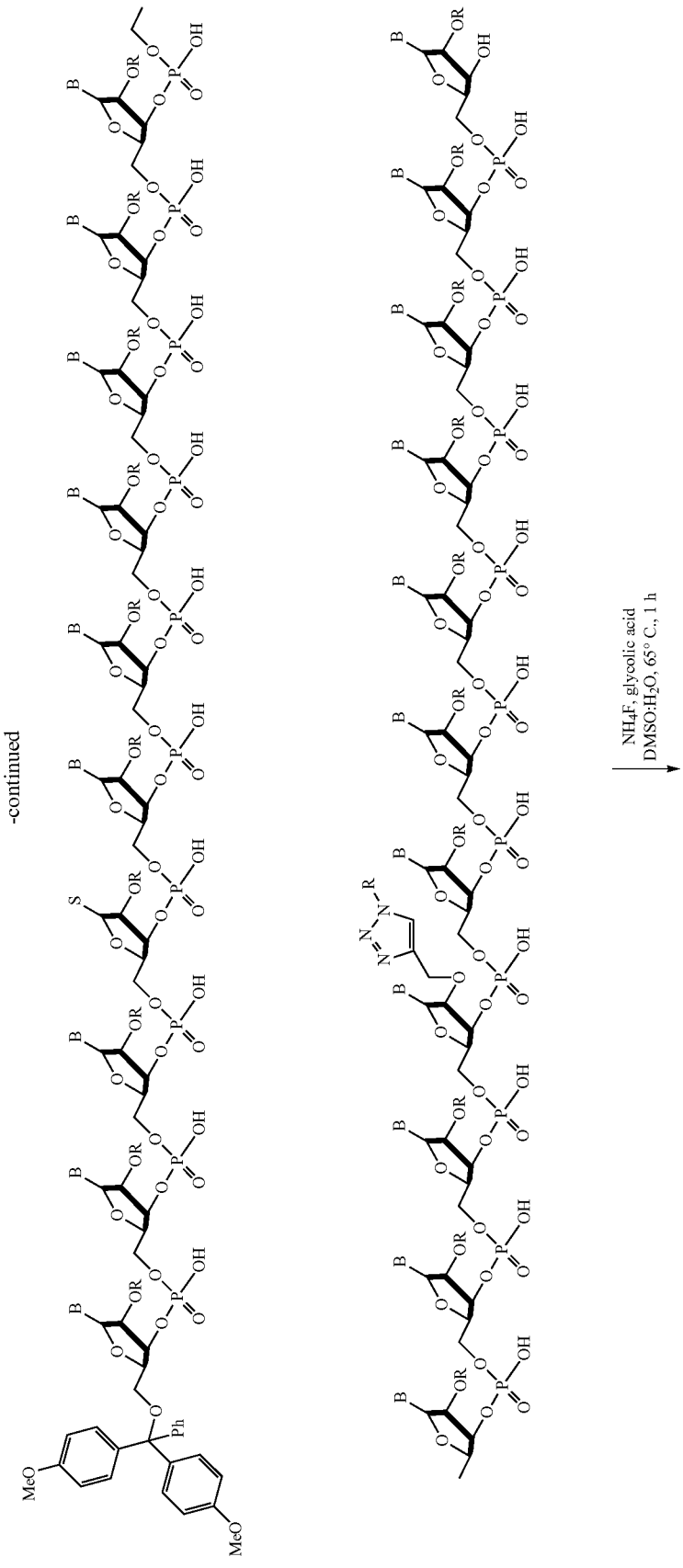

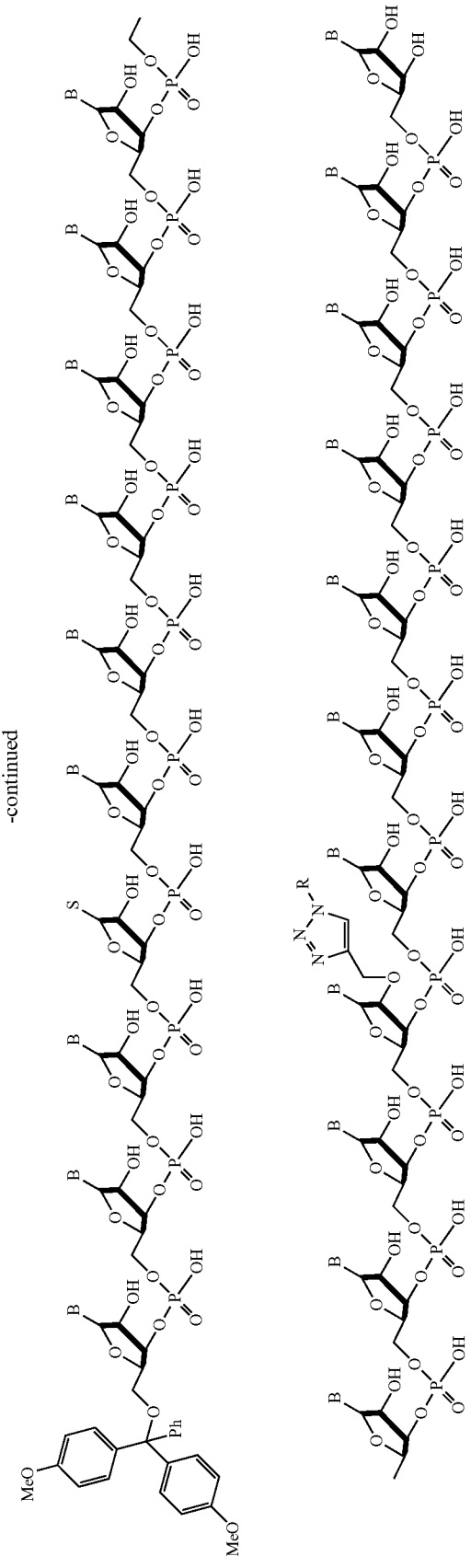
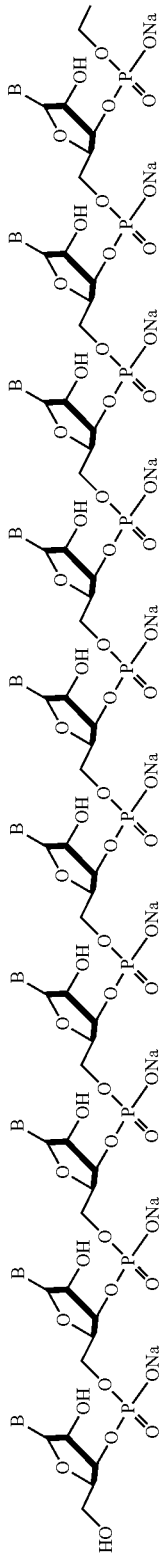
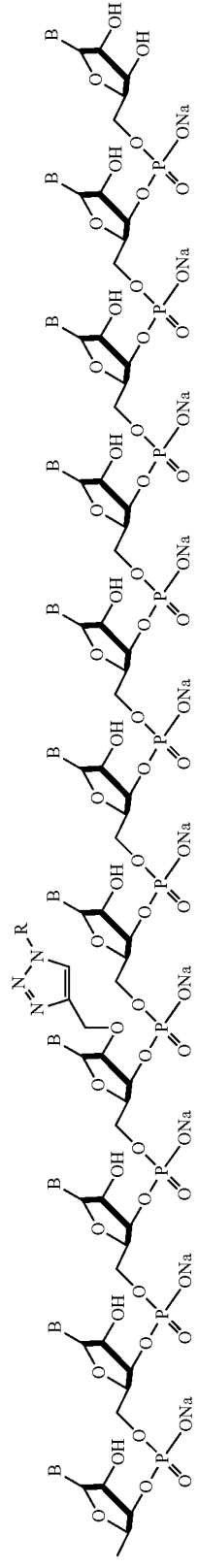
R = TBS protecting group

Click Reaction Between benzyl azide and RNA.

Lyophilized crude RNA (~50 nmol) containing at least one alkyne functional group (shown below) in 96-well format was dissolved in DMSO:water (75:25, 40 µL). Benzyl azide (1M in DMSO, 40 µL) was added, followed by a freshly prepared solution of $CuBr.Me_2S$ in DMSO (12 mM, 40 µL). The reaction block was sealed and heated at 65-80° C. overnight. The solution was cooled to room temperature and ammonium fluoride (100 µL, 5.4M in water) was added. The solution was heated at 65° C. for 1 h, cooled to room temperature and diluted with 1M aqueous NaCl (800 µL). The crude product was purified on a C18 cartridge to afford the desired chemically modified benzyl-triazole-linked RNA as determined by HPLC and LC-MS analyses.

SCHEME 2

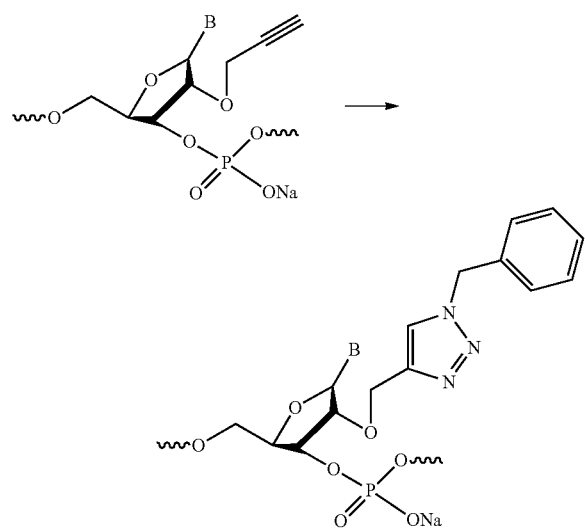

Click Reaction Between azidomethyl phenyl sulfide and RNA.

Crude RNA (~50 nmol) containing at least one alkyne functional group (shown below) was dissolved in DMSO:water (75:25, 40 µL). Azidomethyl phenyl sulfide (1M in DMSO, 40 µL) was added, followed by a freshly prepared solution of $CuBr.Me_2S$ in DMSO (12 mM, 40 µL). The reaction block was sealed and heated to 65-80° C. overnight. The solution was cooled to room temperature and ammonium fluoride (100 µL, 5.4M in water) was added. The solution was heated at 65° C. for 1 h, cooled to room temperature and diluted with 1M aqueous NaCl (800 µL). The crude product was purified on a C18 cartridge to afford the desired chemically modified phenylthiomethyl-triazole-linked RNA as determined by HPLC and LC-MS analyses.

SCHEME 3

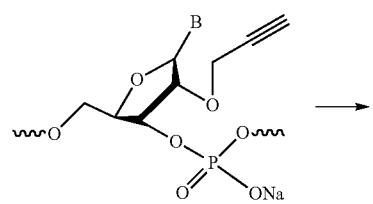

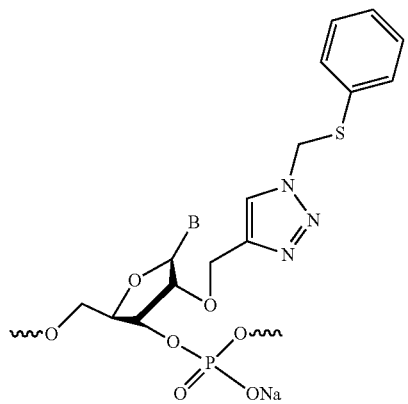

Click Reaction Between ethyl azidoacetate and RNA.

Crude RNA (~50 nmol) containing at least one alkyne functional group (shown below) was dissolved in DMSO:water (75:25, 40 µL). Ethyl azidoacetate (1M in DMSO, 40 µL) was added, followed by a freshly prepared solution of $CuBr.Me_2S$ in DMSO (12 mM, 40 µL). The reaction block was sealed and heated to 65-80° C. overnight. The solution was cooled to room temperature and ammonium fluoride (100 µL, 5.4M in water) was added. The solution was heated at 65° C. for 1 h, cooled to room temperature and diluted with 1M aqueous NaCl (800 µL). The crude product was purified on a C18 cartridge to afford the desired chemically modified ethyl-carboxymethyl-1,4-triazole-linked RNA as determined by HPLC and LC-MS analyses.

SCHEME 4

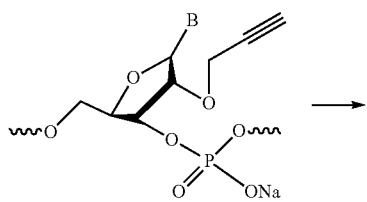

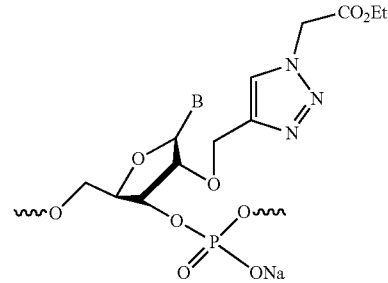

Click Reaction Between N-acetylgalactosamine azide and RNA.

Crude RNA (~50 nmol) containing at least one alkyne functional group (shown below) was dissolved in DMSO: water (75:25, 40 µL). Modified N-acetyl galactosamine azide (1M in DMSO, 40 µL) was added, followed by a freshly prepared solution of CuBr.Me$_2$S in DMSO (12 mM, 40 µL). The reaction block was sealed and heated to 65-80° C. overnight. The solution was cooled to room temperature and ammonium fluoride (100 µL, 5.4M in water) was added. The solution was heated at 65° C. for 1 h, cooled to room temperature and diluted with 1M aqueous NaCl (800 µL). The crude product was purified on a C18 cartridge to afford the desired chemically modified N-acetylgalactosamine-1,4-triazole-linked RNA as determined by HPLC and LC-MS analyses.

SCHEME 5

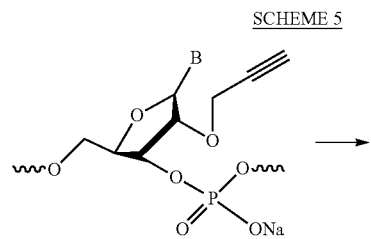

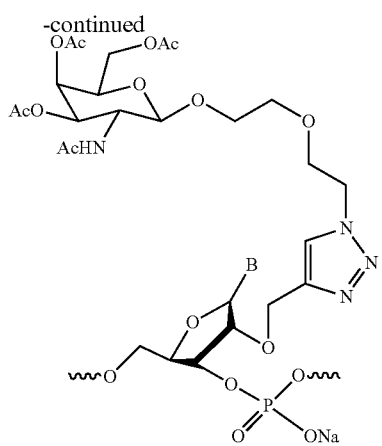

Click Reaction Between N-acetylgalactosamine azide and RNA (Multi-click).

Crude RNA (~50 nmol) containing more than one alkyne functional group (shown below) was dissolved in DMSO: water (75:25, 40 µL). Modified N-acetylgalactosamine azide (1M in DMSO, 40 µL) was added, followed by a freshly prepared solution of CuBr.Me$_2$S in DMSO (12 mM, 40 µL). The reaction block was sealed and heated to 65-80° C. overnight. The solution was cooled to room temperature and ammonium fluoride (100 µL, 5.4M in water) was added. The solution was heated at 65° C. for 1 h, cooled to room temperature and diluted with 1M aqueous NaCl (800 µL). The crude product was purified on a C18 cartridge to afford the desired chemically modified N-acetylgalactosamine-1,4-triazole-linked RNA as determined by HPLC and LC-MS analyses.

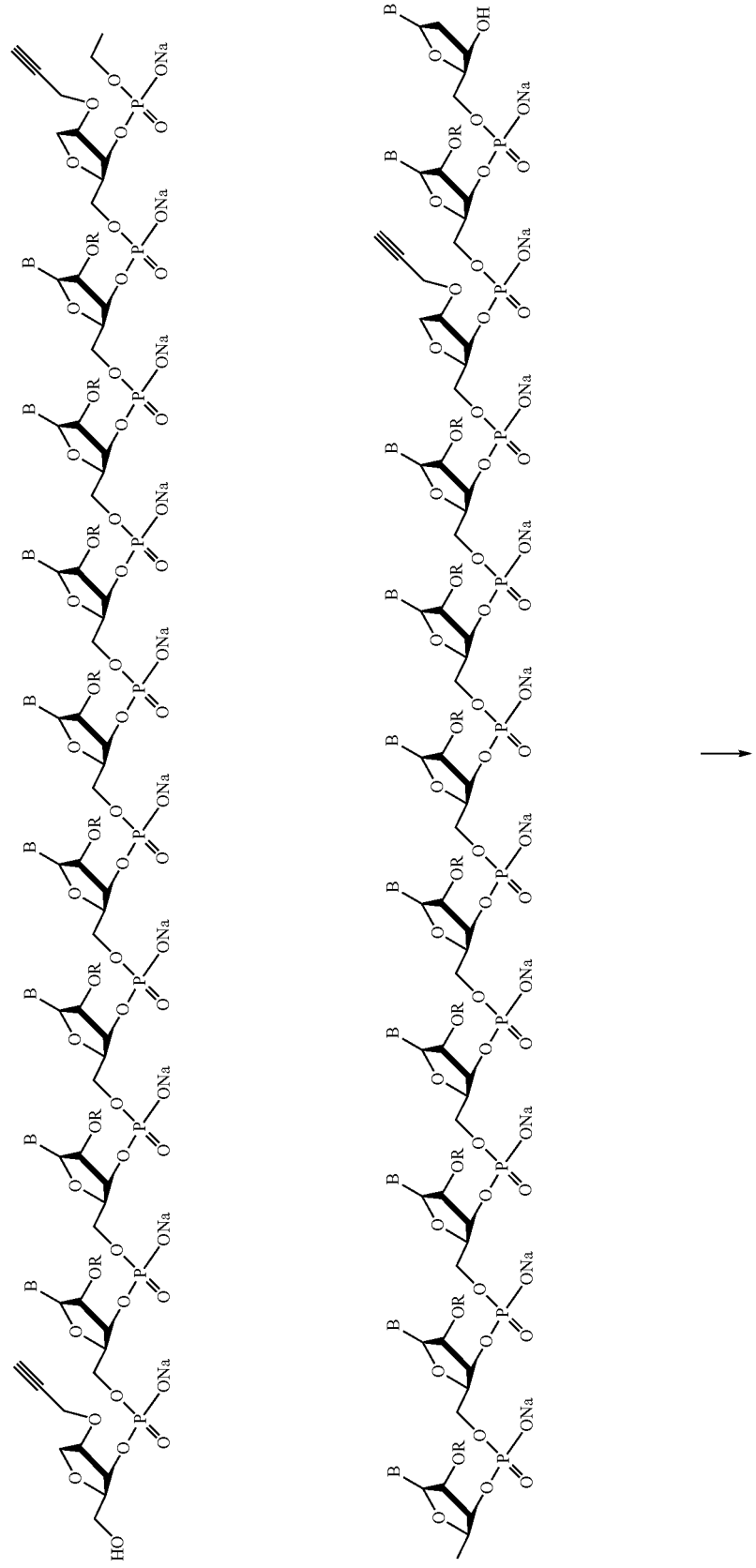

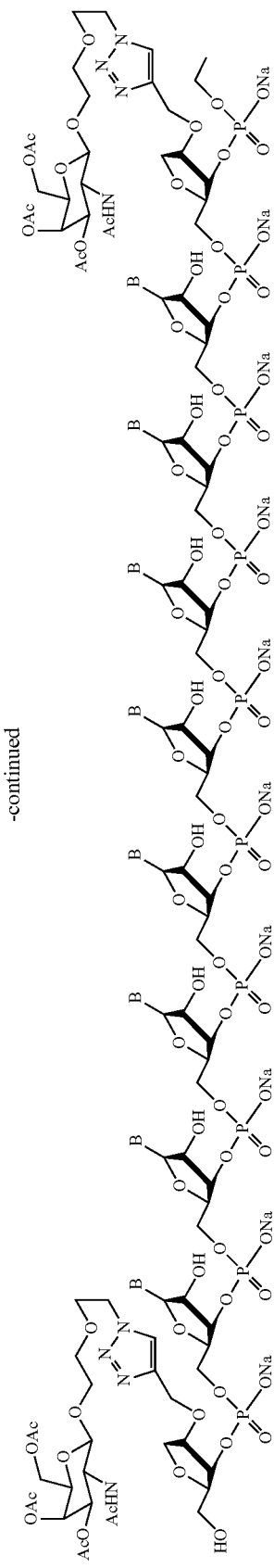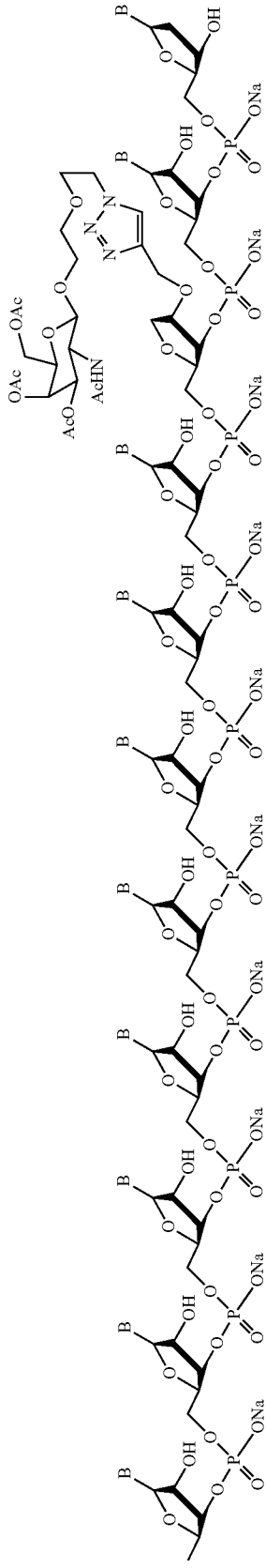
R = TBS

Click Reaction Walkthrough Between benzyl azide and SSB(291) RNA.

Crude RNA (50 nmol) containing at least one alkyne functional group (shown below) was dissolved in DMSO:water (75:25, 40 uL). Benzyl azide (1M in DMSO, 40 uL) was added, followed by a freshly prepared solution of CuBr.Me$_2$S in DMSO (12 mM, 40 uL). The reaction block was sealed and heated at 65-80° C. overnight. The solution was cooled to room temperature and ammonium fluoride (100 μL, 5.4M in water) was added. The solution was heated at 65° C. for 1 h, cooled to room temperature and diluted with 1M aqueous NaCl (800 uL). The crude product was purified on a C18 cartridge to afford the desired chemically modified benzyl-1,4-triazole-linked RNA as determined by HPLC and LC-MS analyses.

SCHEME 7

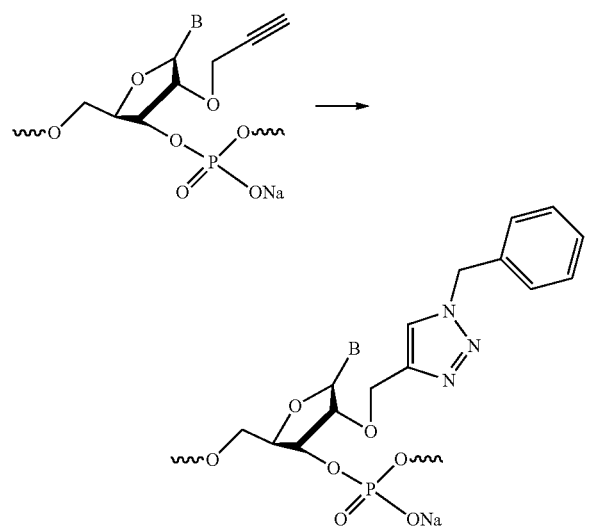

Click Reaction Between 11-azido-3,6,9-trioxaundecan-1-amine and SSB(291) RNA.

Crude RNA (50 nmol) containing at least one alkyne functional group (shown below) was dissolved in DMSO:water (75:25, 40 uL). 11-Azido-3,6,9-trioxaundecan-1-amine (1M in DMSO, 40 uL) was added, followed by a freshly prepared solution of CuBr.Me$_2$S in DMSO (12 mM, 40 uL). The reaction block was sealed and heated at 65-80° C. overnight. The solution was cooled to room temperature and ammonium fluoride (100 μL, 5.4M in water) was added. The solution was heated at 65° C. for 1 h, cooled to room temperature and diluted with 1M aqueous NaCl (800 uL). The crude product was purified on a C18 cartridge to afford the desired chemically modified amino-PEG-1,4-triazole-linked RNA as determined by HPLC and LC-MS analyses.

SCHEME 8

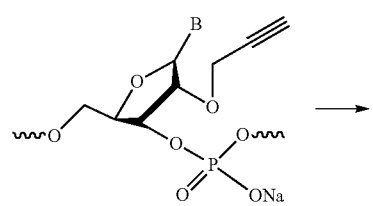

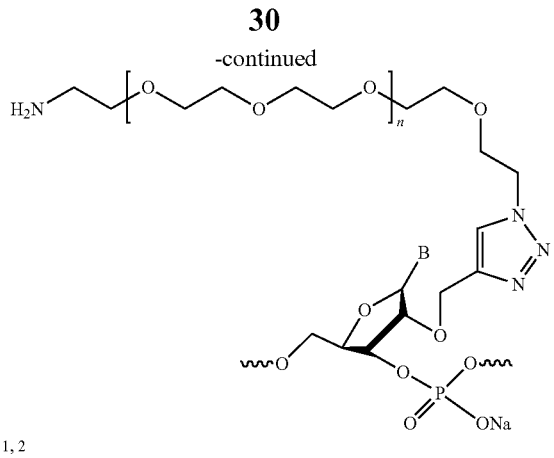

n = 1, 2

Click Reaction on Unprotected "Free" RNA.

Purified deprotected free RNA (8.6 mg, sequence=UUA CAU UAA (2'-propargylabasic) GU CUG UUG UdTdT) (SEQ ID NO: 1) was dissolved in DMSO:water (75:25, 1 mL). The solution (75 μL) was dispensed in wells containing stir bars. A bright blue-green solution (75 μL) of tris(1-(O-ethylcarboxymethyl)-1H-1,2,3-triazol-4-ylmethyl)amine ligand (50 mg) and CuBr (10 mg, 99.999%) in DMSO:water (75:25, 5 mL) was added. Phenylthiomethyl azide (5 μL) was added. The reaction block was sealed and agitated overnight at room temperature. The crude product was purified to afford the desired chemically modified phenyl-thiomethyl-1,4-triazole-linked RNA as determined by HPLC and LC-MS analyses.

SCHEME 9

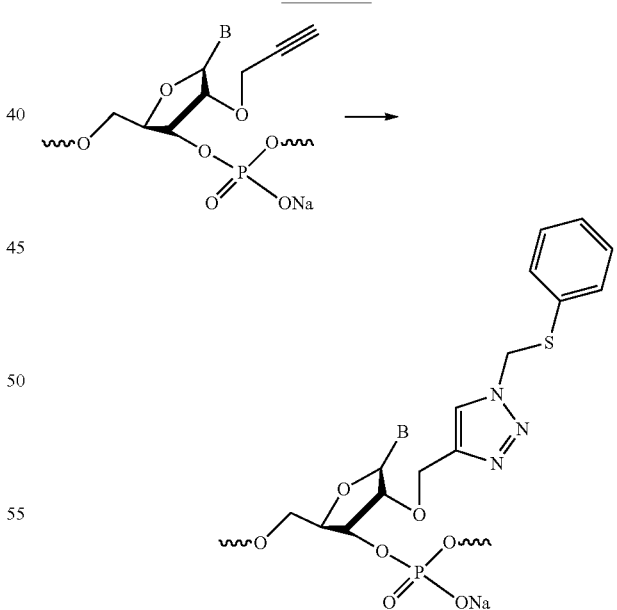

Click Reaction on Unprotected "Free" RNA

Purified deprotected free RNA (8.6 mg, sequence=UUA CAU UAA (2'-propargylabasic) GU CUG UUG UdTdT) (SEQ ID NO: 1) was dissolved in DMSO:water (75:25, 1 mL). The solution (75 μL) was dispensed in wells containing stir bars. A bright blue-green solution (75 μL) of tris(1-(O-ethylcarboxymethyl)-1H-1,2,3-triazol-4-ylmethyl)amine ligand (50 mg) and CuBr (10 mg, 99.999%) in DMSO:water (75:25, 5 mL) was added. Benzyl azide (5 μL) was added. The reaction block was sealed and agitated overnight at room temperature. The crude product was purified to afford the desired chemically modified benzyl-1,4-triazole-linked RNA as determined by HPLC and LC-MS analyses.

SCHEME 10

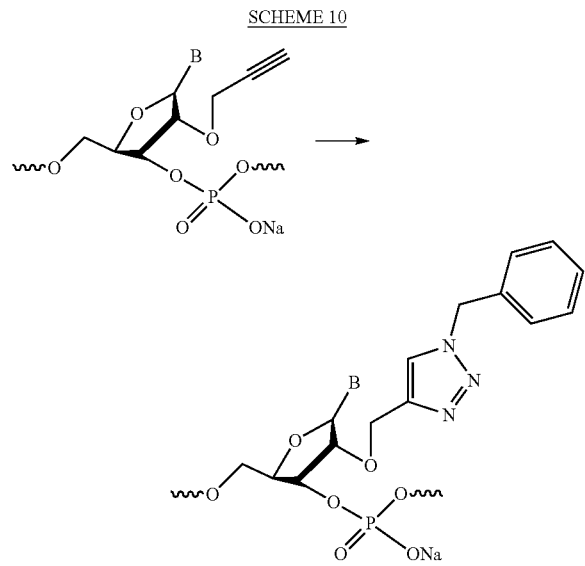

Click Reaction on Unprotected "Free" RNA

Purified deprotected free RNA (8.6 mg, sequence=UUA CAU UAA (2'-propargylabasic) GU CUG UUG UdTdT) (SEQ ID NO: 1) was dissolved in DMSO:water (75:25, 1 mL). The solution (75 μL) was dispensed in wells containing stir bars. A bright blue-green solution (75 μL) of tris(1-(O-ethylcarboxymethyl)-1H-1,2,3-triazol-4-ylmethyl)amine ligand (50 mg) and CuBr (10 mg, 99.999%) in DMSO:water (75:25, 5 mL) was added. Ethyl azidoacetate (15 μL, 25-30% wt in EtOH) was added. The reaction block was sealed and agitated overnight at room temperature. The crude product was purified to afford the desired chemically modified ethyl carboxymethyl-1,4-triazole-linked RNA as determined by HPLC and LC-MS analyses.

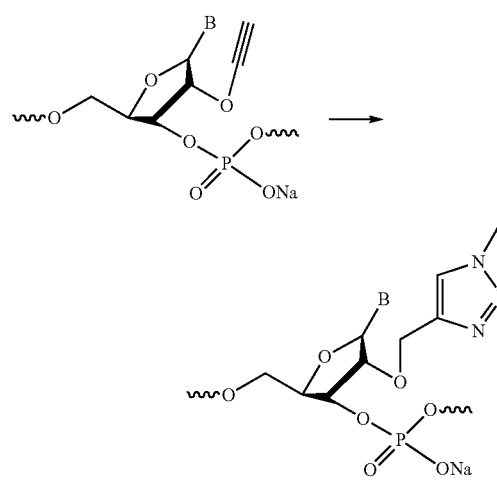

Assays

| Gene | Position in mRNA sequence | Guide strand sequence (5'-3') | SEQ ID NO |
|------|---------------------------|-------------------------------|-----------|
| SSB  | 291                       | UUACAUUAAAGUCUGUUGU           | 2         |
| Luc  | 80                        | UAUCUCUUCAUAGCCUUAU           | 3         |

Positions 1-19 of both strands were ribonucleotides, and the overhangs at positions 20 and 21 contained 2'-deoxyribonucleotide thymidines. This unmodified siRNA was the template for systematic evaluation of modified siRNAs containing a single modification at every position along the guide strand. In order to examine the effect of the chemical modifications for the SSB sequence, we synthesized the RNA oligomers with the first nucleotide, uridine (U), replaced with 2'-O-propargyl-inosine. Then, a second sequence, in which the second nucleoside (U) was replaced with 2'-O-propargyl-inosine was synthesized, keeping all other nucleotides unchanged. Altogether nineteen sequences were synthesized where the universal base replaced all the natural nucleosides in that sequence. This "modification walkthrough" is depicted in Table 1 for SSB(291). The desired chemical modification was then introduced into the assembled RNA by the methods described in Schemes 6 and 7.

TABLE 1

| Entry | Gene | Position in mRNA sequence | Guide strand sequence (5'-3') | SEQ ID NO |
|-------|------|---------------------------|-------------------------------|-----------|
| unmodified | SSB | 291 | UUACAUUAAAGUCUGUUGU | 2 |
| 1  | SSB | 291 | NUACAUUAAAGUCUGUUGU | 4 |
| 2  | SSB | 291 | UNACAUUAAAGUCUGUUGU | 5 |
| 3  | SSB | 291 | UUNCAUUAAAGUCUGUUGU | 6 |
| 4  | SSB | 291 | UUANAUUAAAGUCUGUUGU | 7 |
| 5  | SSB | 291 | UUACNUUAAAGUCUGUUGU | 8 |
| 6  | SSB | 291 | UUACANUAAAGUCUGUUGU | 9 |
| 7  | SSB | 291 | UUACAUNAAAGUCUGUUGU | 10 |
| 8  | SSB | 291 | UUACAUUNAAGUCUGUUGU | 11 |
| 9  | SSB | 291 | UUACAUUANAGUCUGUUGU | 12 |
| 10 | SSB | 291 | UUACAUUAANGUCUGUUGU | 13 |
| 11 | SSB | 291 | UUACAUUAAANUCUGUUGU | 14 |
| 12 | SSB | 291 | UUACAUUAAAGNCUGUUGU | 15 |
| 13 | SSB | 291 | UUACAUUAAAGUNUGUUGU | 16 |
| 14 | SSB | 291 | UUACAUUAAAGUCNGUUGU | 17 |
| 15 | SSB | 291 | UUACAUUAAAGUCUNUUGU | 18 |
| 16 | SSB | 291 | UUACAUUAAAGUCUGNUGU | 19 |
| 17 | SSB | 291 | UUACAUUAAAGUCUGUNGU | 20 |

TABLE 1-continued

| Entry | Gene | Position in mRNA sequence | Guide strand sequence (5'-3') | SEQ ID NO |
|---|---|---|---|---|
| 18 | SSB | 291 | UUACAUUAAAGUCUGUUNU | 21 |
| 19 | SSB | 291 | UUACAUUAAAGUCUGUUGN | 22 |

(N represents a universal base such as inosine)

SSB Knockdown

In a 96-well format, Hepal-6 cells were transfected with 10 nM of either the unmodified, modified, or negative control siRNA using a commercial lipid transfection reagent. The target mRNA was assessed for degradation using standard Taqman procedures.

Modified Multiplex Luciferase Report Assay for in vitro Duration Study

Assay Principle:

Multiplex luciferase assay for in vitro duration study is modified from the manufacturer's instruction using HeLa-luc cell line. Briefly, the cell viability and the luciferase expression at the same well are determined by CellTiter-Fluor™ (Promega, Cat# G6082) and Bright-Glo™ (Promega Cat# E2620) sequentially.

HeLa-luc cell line is a stable firefly luciferase reporter expression cell line. Bright-Glo™ luciferase assay system contains the stable substrate—luciferin and assay buffer. The luminescent reaction of luciferase and luciferin has high quantum yield and can be detected as luminescence intensity, which represents the luciferase expression level.

Target siRNAs containing luciferase coding region is designed to be transfected into the HeLa-luc cells. Once the target is effected, the luciferase expression is reduced accordingly, Therefore, the siRNA silencing efficacy can be determined by the relative luminescence intensity of treated cells.

To reduce the variation caused by cell viability and cell plating process, the cell viability of the same treatment wells is measured using CellTiter-fluor kit. This assay measures the conserved and constitutive protease activity within live cells and therefore serves as a marker of cell viability, using a fluorogenic, cell-permeable peptide substrate (glycyl-phenylalanyl-aminofluorocoumarin; GF-AFC).

Experiment Design:

Luciferase stable expressed HeLa-luc cell cells are plated in 96-well plates at density of 4,500 cells per well in 100 μL DMEM media without antibiotics 24 hours prior to transfection. siRNA transfection is performed using the RNAiMAX™ (Invitrogen). Briefly, 0.05 μM siRNA are mixed with Opti-MEMmedia and RNAiMAX and incubated at room temperature for 15 min. The mix is then added to the cells. The final siRNA concentration is 1 nM. Cell plates for all time points are transfected at same time with a medium change at 6 hours post-transfection into 100 μL of fresh completed DMEM (DMEM+10% FBS+Pen/strep).

In vitro duration is determined by the luciferase expression post-transfection at four time points: day 1, day 2, day 5 and day 7. Addition medium changes are performed at day 2 and day 5 into 100 μL of fresh completed DMEM (DMEM+10% FBS+Penn/strep). Luciferase levels are determined using the Bright-Glo Luminescence Assay (Promega) and measuring the wells on an Envison instrument (Perkin Elmer) according to manufacturer's instructions.

To reduce the variation caused by cell viability and cell plating process, the cell viability of the same treatment wells is measured using CellTiter-fluor kit (Promega) according to manufacturer's instructions. This assay measures the conserved and constitutive protease activity within live cells and therefore servers as a marker of cell viability, using a fluorogenic, cell-permeable peptide substrate (glycyl-phenylalanyl-aminofluorocoumarin; GF-AFC). The fluorescence was measured on the Envision using exciton filter at 405 nm and emission filter at 510 nm.

The luciferase expression was normalized to cell viability. The log of this number was calculated to determine the luciferase protein that was degraded (knockdown). A non-targeting siRNA was subtracted from this value to account for non-specific background.

EXAMPLES

The following Examples 1-6 were generated utilizing the Assays above and demonstrate the utility of the RNAs made by the methods described in the Schemes. As demonstrated, the RNAs made by the process of the invention are useful in high-throughput structure-activity relationship studies on chemically modified RNA in 96-well format.

Example 1

In FIG. 1, the impact on knockdown of the 2'-O-benzyl-triazole inosine chemical modification was systematically evaluated along positions 1 through 19 of the guide strand of an siRNA targeting mRNA SSB(291).

Example 2

Figure 2:
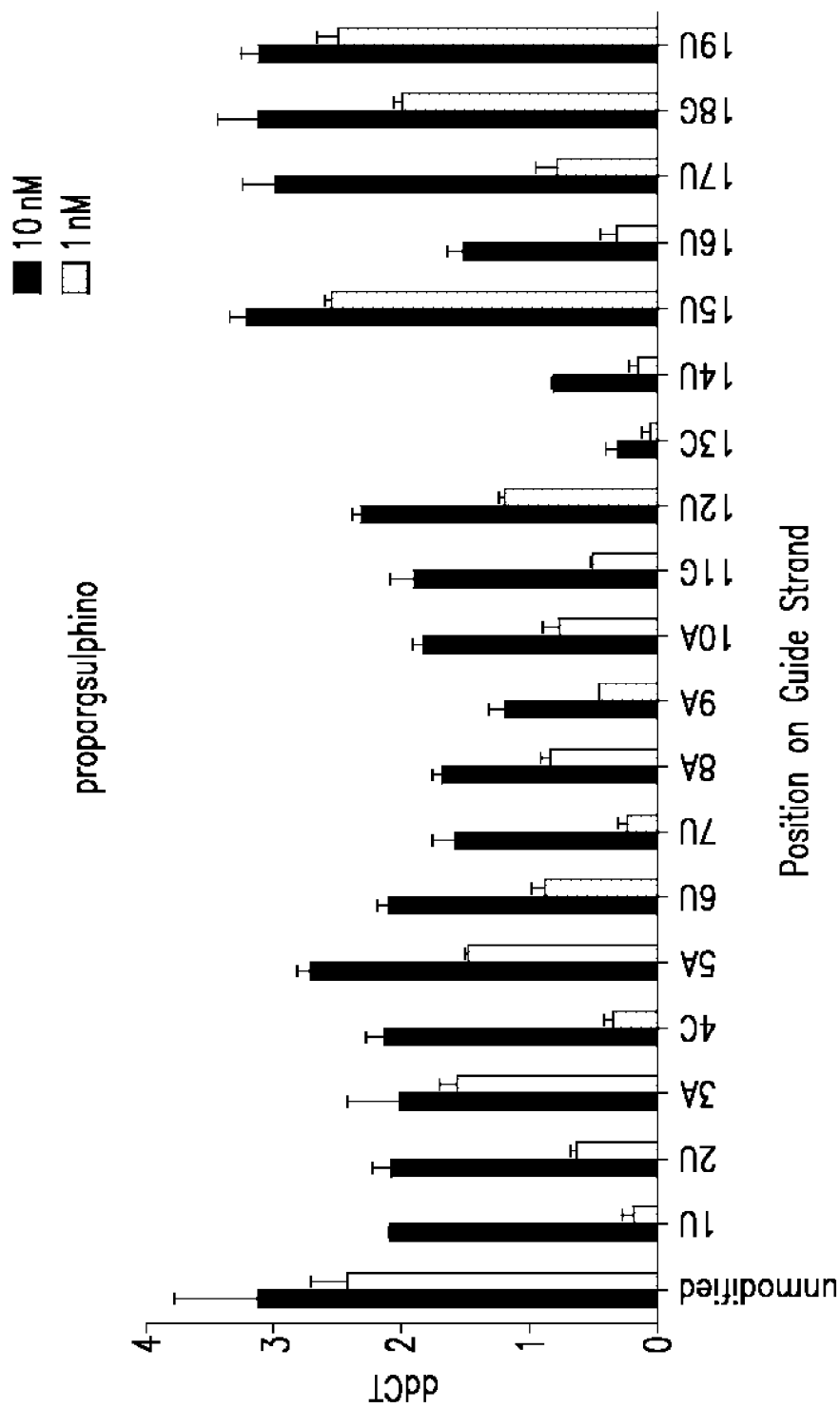
FIG. 2. Systematic evaluation of the impact on knockdown of the 2'-O-phenylthiomethyl-triazole inosine chemical modification along positions 1 through 19 of the guide strand of a SSB(291) siRNA.

In FIG. 2, the impact of the 2'-O-phenylthiomethyl-triazole inosine chemical modification was systematically evaluated along positions 1 through 19 of the guide strand of an siRNA targeting mRNA SSB(291).

Example 3

Figure 3:
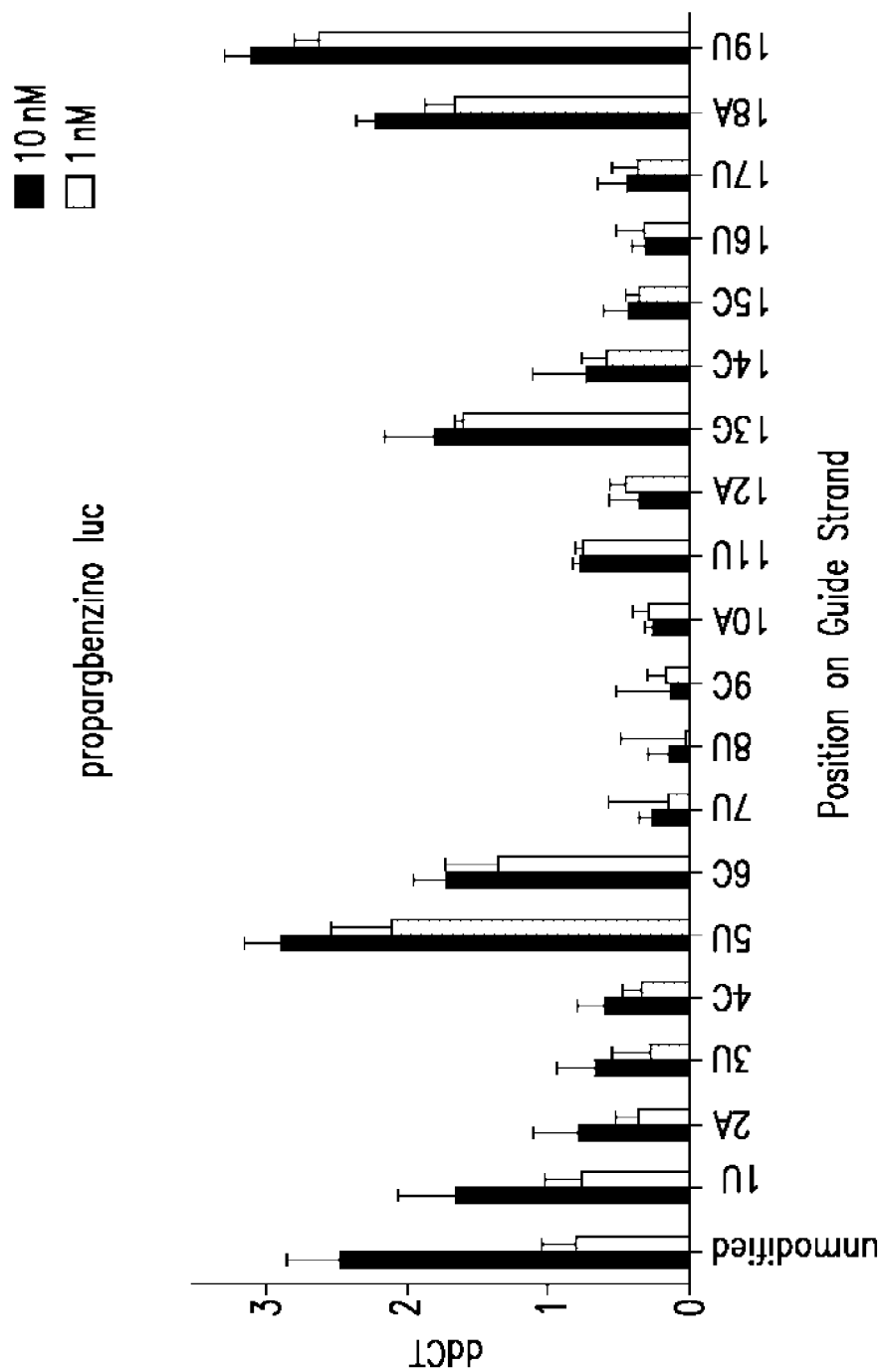
FIG. 3. Systematic evaluation of the impact on knockdown of the 2'-O-benzyl-triazole inosine chemical modification was systematically evaluated along positions 1 through 19 of the guide strand of a Luc(80) siRNA.

In FIG. 3, the impact on knockdown of the 2'-O-benzyl-triazole inosine chemical modification was systematically evaluated along positions 1 through 19 of the guide strand of an siRNA targeting mRNA Luc(80).

Example 4

Figure 4:
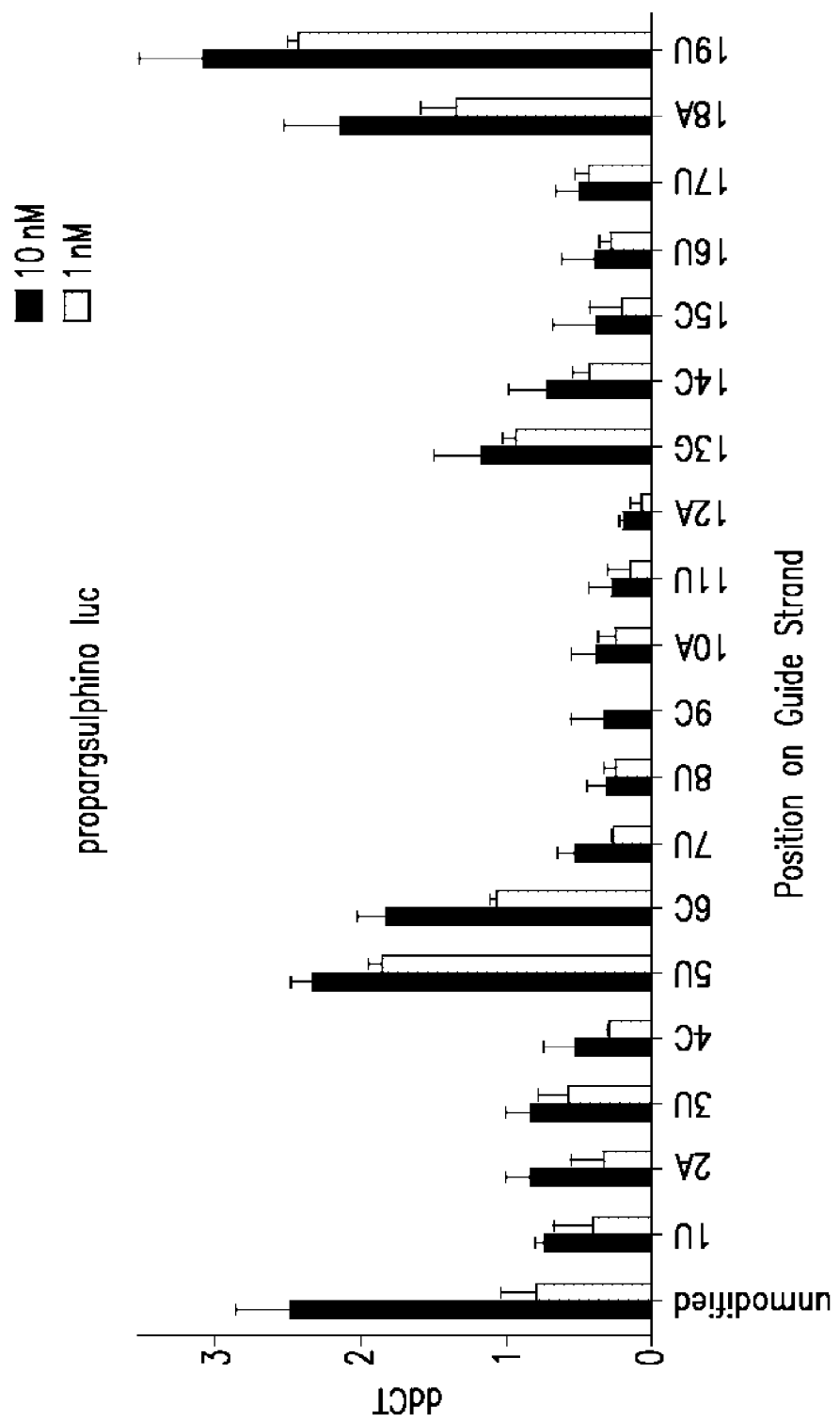
FIG. 4. Systematic evaluation of the impact on knockdown of the 2'-O-phenylthiomethyl-triazole inosine chemical modification was systematically evaluated along positions 1 through 19 of the guide strand of a Luc(80) siRNA.

In FIG. 4, the impact of the 2'-O-phenylthiomethyl-triazole inosine chemical modifications were systematically evaluated along positions 1 through 19 of the guide strand of an siRNA targeting mRNA Luc(80).

Example 5

Figure 5:
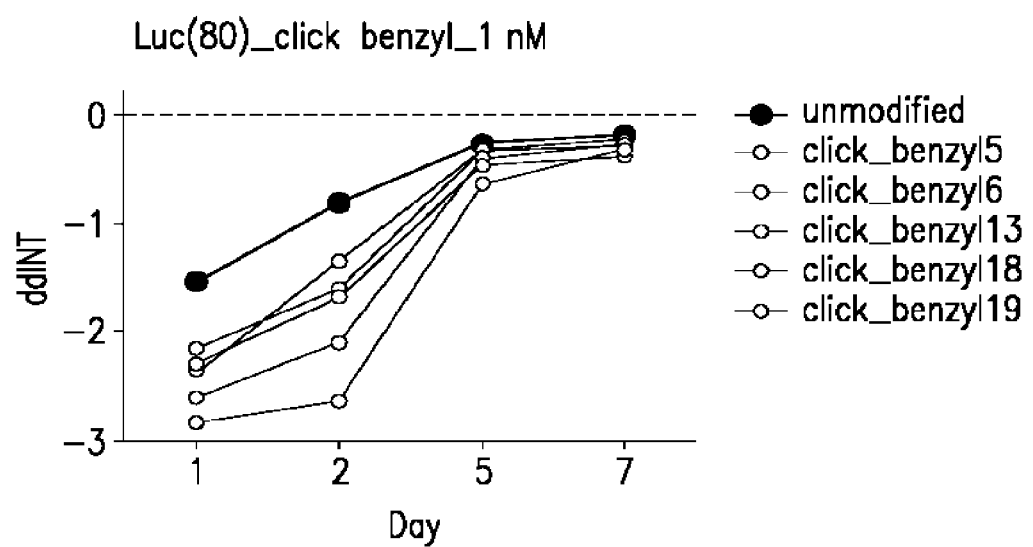
FIG. 5. Duration of knockdown activity of the 2'-O-benzyl-triazole inosine chemical modification was systematically evaluated along positions 1 through 19 of the guide strand of a Luc(80) siRNA.

In FIG. 5, the impact on duration of knockdown activity of the 2'-O-benzyl-triazole inosine chemical modification was systematically evaluated along positions 1 through 19 of the guide strand of an siRNA targeting mRNA Luc(80).

Example 6

Figure 6:
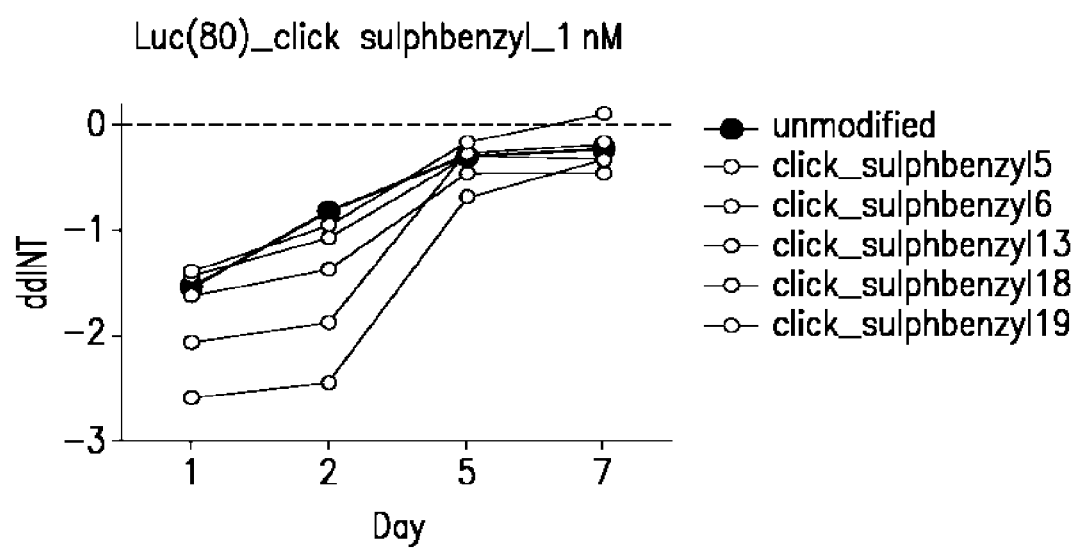
FIG. 6. Duration of knockdown activity of the 2'-O-phenylthiomethyl inosine chemical modification was systematically evaluated along positions 1 through 19 of the guide strand of a Luc(80) siRNA.

In FIG. 6, the impact on duration of knockdown activity of the 2'-O-phenylthiomethyl inosine chemical modification was systematically evaluated along positions 1 through 19 of the guide strand of an siRNA targeting mRNA Luc(80).

Example 7

Figure 7:
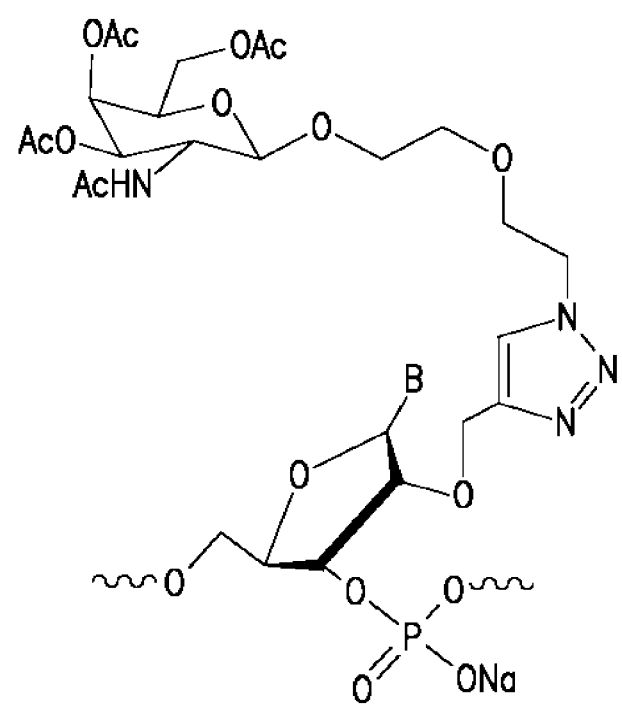
FIG. 7. Introduction of N-acetyl-galactosamine as chemical modification.

In FIG. 7, the liver targeting compound N-acetyl-galactosamine (NAG) can be introduced as a chemical modification that may help with specific cell targeting, cellular uptake and delivery of RNA.

Example 8

Figure 8:
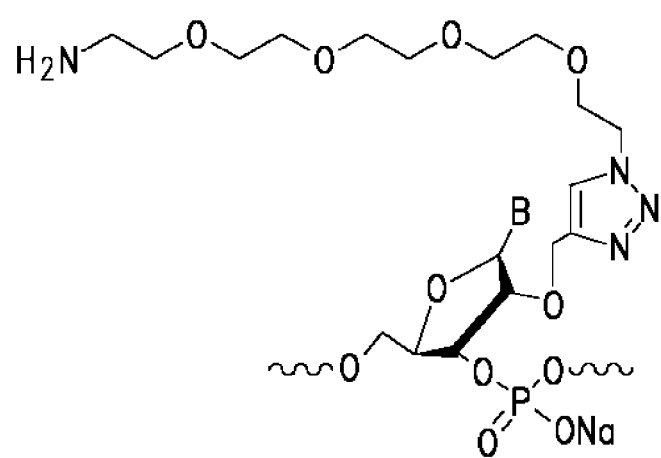
FIG. 8. Introduction of poly(ethylene)glycol amine in SSB(291) RNA.

In FIG. 8, poly(ethylene)glycol amines can be introduced to improve solubility properties, cellular uptake, immune stealth, reduce metabolic clearance and delivery of RNA.

Example 9

Figure 9:
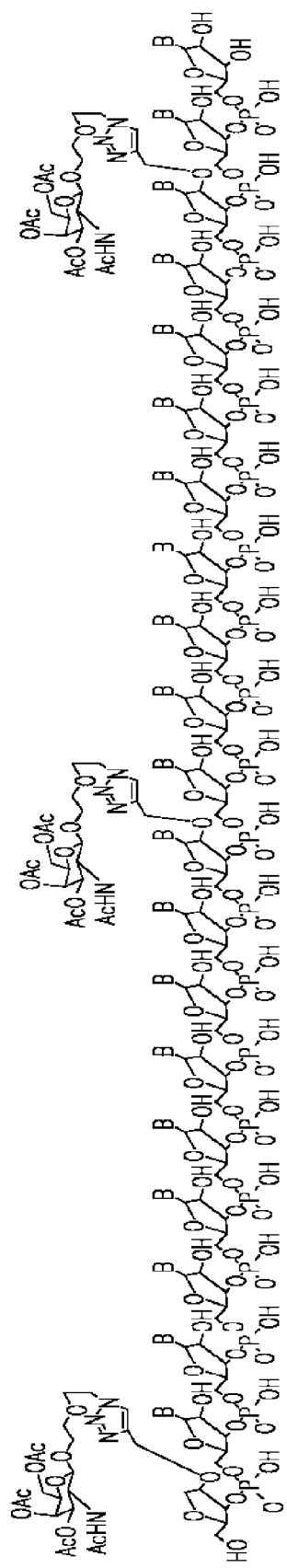
FIG. 9. Multi-click for introduction of multiple N-acetyl-galactosamine chemical modifications in one synthetic operation.

In FIG. 9, the "click" reaction can be utilized to introduce multiple chemical modifications in one synthetic operation. For example, the click reaction was performed to introduce three units of protected N-acetylgalactosamine on RNA. This may lead to improved physical properties towards solubility, cellular uptake, and delivery of siRNA.

What is claimed is:

1. A 2'-modified siRNA, comprising at least one RNA strand containing a 2'-O substituent having an alkyne functional group at the 2'-position on one or more ribose rings, wherein the 2'-O substituent is located at one or more of positions 2, 3, 4, 7, 8, 9, 10, 11, 13, 14, and 16, from 5'-end of the RNA strand.

2. The 2'-modified siRNA of claim 1, wherein the 2'-O substituent is located at one or more of positions 4, 9, 13, and 14.

3. The 2'-modified siRNA of claim 1, wherein the 2'-O substituent is located at one or more of positions 7, 8, 9, and 10.

4. The 2'-modified siRNA of claim 1, wherein the RNA strand contains a 2'-O substituent having an alkyne functional group at the 2'-position on two or more ribose rings.

5. The 2'-modified siRNA of claim 1, wherein the siRNA is a miRNA (micro RNA).

6. The 2'-modified siRNA of claim 1, wherein the siRNA comprises a guide (antisense) strand, and the 2'-O substituent is contained in the guide strand.

7. The 2'-modified siRNA of claim 1, wherein the siRNA comprises a passenger (sense) strand, and the 2'-O substituent is contained in the passenger strand.

8. The 2'-modified siRNA agent of claim 1, wherein the RNA strand has a length of about 19 to 21 nucleotides.

9. The 2'-modified RNA agent of claim 1, wherein the alkyne functional group is a propargyl moiety attaching to the oxygen atom of the 2'-O substituent.

10. A 2'-modified siRNA, comprising at least one RNA strand containing a 2'-O substituent having a triazole functional group at the 2'-position on one or more ribose rings, wherein the 2'-O substituent is located at one or more of positions 2, 3, 4, 7, 8, 9, 10, 11, 13, 14, and 16, from 5'-end of the RNA strand.

11. The 2'-modified siRNA of claim 10, wherein the 2'-O substituent is located at one or more of positions 4, 9, 13, and 14.

12. The 2'-modified siRNA of claim 10, wherein the 2'-O substituent is located at one or more of positions 7, 8, 9, and 10.

13. The 2'-modified siRNA of claim 10, wherein the RNA strand contains a 2'-O substituent having a triazole functional group at the 2'-position on two or more ribose rings.

14. The 2'-modified siRNA of claim 10, wherein the RNA strand contains a 2'-O substituent having a triazole functional group at the 2'-position on three or more ribose rings.

15. The 2'-modified siRNA of claim 10, wherein the siRNA comprises a guide (antisense) strand, and the 2'-O substituent is contained in the guide strand.

16. The 2'-modified siRNA of claim 10, wherein the siRNA comprises a passenger (sense) strand, and the 2'-O substituent is contained in the passenger strand.

17. The 2'-modified siRNA of claim 10, wherein the triazole functional group further comprises a lipid, sugar, protein, peptide, poly(ethylene)glycols, or antibody moiety.

18. The 2'-modified siRNA of claim 10, wherein the triazole functional group further comprises benzyl or modified benzyl, ethyl-carboxymethyl, N-acetylgalactosamine, or PEG or amino-PEG.

* * * * *

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: synthetic

<400> SEQUENCE: 1
uuacauuaag ucuguugudt dt                                               22

<210> SEQ ID NO 2
<211> LENGTH: 19
<212> TYPE: DNA
<213> ORGANISM: Artificial Sequence
<220> FEATURE:
<223> OTHER INFORMATION: synthetic

<400> SEQUENCE: 2
uuacauuaaa gucuguugu                                                   19

<210> SEQ ID NO 3
<211> LENGTH: 19
<212> TYPE: DNA
<213> ORGANISM: Artificial Sequence
<220> FEATURE:
<223> OTHER INFORMATION: synthetic

<400> SEQUENCE: 3
uaucucuuca uagccuuau                                                   19

<210> SEQ ID NO 4
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 1
<223> OTHER INFORMATION: ribonucleotide unmodified or modified as
      described for this sequence
<221> NAME/KEY: misc_feature
<222> LOCATION: 1
<223> OTHER INFORMATION: n = A,T,C or G

<400> SEQUENCE: 4
nuacauuaaa gucuguugu                                                   19

<210> SEQ ID NO 5
<211> LENGTH: 19
<212> TYPE: DNA
<213> ORGANISM: Artificial Sequence
```

-continued

```
<220> FEATURE:
<223> OTHER INFORMATION: synthetic
<221> NAME/KEY: misc_feature
<222> LOCATION: 2, 4
<223> OTHER INFORMATION: ribonucleotide unmodified or modified as
      described for this sequence
<221> NAME/KEY: misc_feature
<222> LOCATION: 2, 4
<223> OTHER INFORMATION: n = A,T,C or G

<400> SEQUENCE: 5
unanauuaaa gucuguugu                                                19

<210> SEQ ID NO 6
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 3, 5
<223> OTHER INFORMATION: ribonucleotide unmodified or modified as
      described for this sequence
<221> NAME/KEY: misc_feature
<222> LOCATION: 3, 5
<223> OTHER INFORMATION: n = A,T,C or G

<400> SEQUENCE: 6
uuncnuuaaa gucuguugu                                                19

<210> SEQ ID NO 7
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 4
<223> OTHER INFORMATION: ribonucleotide unmodified or modified as
      described for this sequence
<221> NAME/KEY: misc_feature
<222> LOCATION: 4
<223> OTHER INFORMATION: n = A,T,C or G

<400> SEQUENCE: 7
uuanauuaaa gucuguugu                                                19

<210> SEQ ID NO 8
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 5
<223> OTHER INFORMATION: ribonucleotide unmodified or modified as
      described for this sequence
<221> NAME/KEY: misc_feature
<222> LOCATION: 5
<223> OTHER INFORMATION: n = A,T,C or G

<400> SEQUENCE: 8
uuacnuuaaa gucuguugu                                                19

<210> SEQ ID NO 9
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
```

```
<222> LOCATION: 6
<223> OTHER INFORMATION: ribonucleotide unmodified or modified as
      described for this sequence
<221> NAME/KEY: misc_feature
<222> LOCATION: 6
<223> OTHER INFORMATION: n = A,T,C or G

<400> SEQUENCE: 9
uuacanuaaa gucuguugu                                                    19

<210> SEQ ID NO 10
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 7
<223> OTHER INFORMATION: ribonucleotide unmodified or modified as
      described for this sequence
<221> NAME/KEY: misc_feature
<222> LOCATION: 7
<223> OTHER INFORMATION: n = A,T,C or G

<400> SEQUENCE: 10
uuacaunaaa gucuguugu                                                    19

<210> SEQ ID NO 11
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 8
<223> OTHER INFORMATION: ribonucleotide unmodified or modified as
      described for this sequence
<221> NAME/KEY: misc_feature
<222> LOCATION: 8
<223> OTHER INFORMATION: n = A,T,C or G

<400> SEQUENCE: 11
uuacauunaa gucuguugu                                                    19

<210> SEQ ID NO 12
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 9
<223> OTHER INFORMATION: ribonucleotide unmodified or modified as
      described for this sequence
<221> NAME/KEY: misc_feature
<222> LOCATION: 9
<223> OTHER INFORMATION: n = A,T,C or G

<400> SEQUENCE: 12
uuacauuana gucuguugu                                                    19

<210> SEQ ID NO 13
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 10
<223> OTHER INFORMATION: ribonucleotide unmodified or modified as
      described for this sequence
```

```
<221> NAME/KEY: misc_feature
<222> LOCATION: 10
<223> OTHER INFORMATION: n = A,T,C or G

<400> SEQUENCE: 13
uuacauuaan gucuguugu                                              19

<210> SEQ ID NO 14
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 11
<223> OTHER INFORMATION: ribonucleotide unmodified or modified as
      described for this sequence
<221> NAME/KEY: misc_feature
<222> LOCATION: 11
<223> OTHER INFORMATION: n = A,T,C or G

<400> SEQUENCE: 14
uuacauuaaa nucuguugu                                              19

<210> SEQ ID NO 15
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 12
<223> OTHER INFORMATION: ribonucleotide unmodified or modified as
      described for this sequence
<221> NAME/KEY: misc_feature
<222> LOCATION: 12
<223> OTHER INFORMATION: n = A,T,C or G

<400> SEQUENCE: 15
uuacauuaaa gncuguugu                                              19

<210> SEQ ID NO 16
<211> LENGTH: 19
<212> TYPE: DNA
<213> ORGANISM: Artificial Sequence
<220> FEATURE:
<223> OTHER INFORMATION: synthetic
<221> NAME/KEY: misc_feature
<222> LOCATION: 13
<223> OTHER INFORMATION: ribonucleotide unmodified or modified as
      described for this sequence
<221> NAME/KEY: misc_feature
<222> LOCATION: 13
<223> OTHER INFORMATION: n = A,T,C or G

<400> SEQUENCE: 16
uuacauuaaa gunuguugu                                              19

<210> SEQ ID NO 17
<211> LENGTH: 19
<212> TYPE: RNA
<213> ORGANISM: Artificial Sequence
<220> FEATURE:
<223> OTHER INFORMATION: synthetic amino acid
<221> NAME/KEY: misc_feature
<222> LOCATION: 14
<223> OTHER INFORMATION: n = a universal base such as inosine
<221> NAME/KEY: misc_feature
<222> LOCATION: 14
<223> OTHER INFORMATION: n = A,T,C or G
```

```
<400> SEQUENCE: 17
uuacauuaaa gucnguugu                                              19

<210> SEQ ID NO 18
<211> LENGTH: 19
<212> TYPE: RNA
<213> ORGANISM: Artificial Sequence
<220> FEATURE:
<223> OTHER INFORMATION: synthetic amino acid
<221> NAME/KEY: misc_feature
<222> LOCATION: 15
<223> OTHER INFORMATION: n = a universal base such as inosine
<221> NAME/KEY: misc_feature
<222> LOCATION: 15
<223> OTHER INFORMATION: n = A,T,C or G

<400> SEQUENCE: 18
uuacauuaaa gucnuugu                                               19

<210> SEQ ID NO 19
<211> LENGTH: 19
<212> TYPE: RNA
<213> ORGANISM: Artificial Sequence
<220> FEATURE:
<223> OTHER INFORMATION: synthetic amino acid
<221> NAME/KEY: misc_feature
<222> LOCATION: 16
<223> OTHER INFORMATION: n = a universal base such as inosine
<221> NAME/KEY: misc_feature
<222> LOCATION: 16
<223> OTHER INFORMATION: n = A,T,C or G

<400> SEQUENCE: 19
uuacauuaaa gucugnugu                                              19

<210> SEQ ID NO 20
<211> LENGTH: 19
<212> TYPE: RNA
<213> ORGANISM: Artificial Sequence
<220> FEATURE:
<223> OTHER INFORMATION: synthetic amino acid
<221> NAME/KEY: misc_feature
<222> LOCATION: 17
<223> OTHER INFORMATION: n = a universal base such as inosine
<221> NAME/KEY: misc_feature
<222> LOCATION: 17
<223> OTHER INFORMATION: n = A,T,C or G

<400> SEQUENCE: 20
uuacauuaaa gucugungu                                              19

<210> SEQ ID NO 21
<211> LENGTH: 19
<212> TYPE: RNA
<213> ORGANISM: Artificial Sequence
<220> FEATURE:
<223> OTHER INFORMATION: synthetic amino acid
<221> NAME/KEY: misc_feature
<222> LOCATION: 18
<223> OTHER INFORMATION: n = a universal base such as inosine
<221> NAME/KEY: misc_feature
<222> LOCATION: 18
<223> OTHER INFORMATION: n = A,T,C or G

<400> SEQUENCE: 21
uuacauuaaa gucuguunu                                              19

<210> SEQ ID NO 22
<211> LENGTH: 19
```

```
<212> TYPE: RNA
<213> ORGANISM: Artificial Sequence
<220> FEATURE:
<223> OTHER INFORMATION: synthetic amino acid
<221> NAME/KEY: misc_feature
<222> LOCATION: 19
<223> OTHER INFORMATION: n = a universal base such as inosine
<221> NAME/KEY: misc_feature
<222> LOCATION: 19
<223> OTHER INFORMATION: n = A,T,C or G

<400> SEQUENCE: 22
uuacauuaaa gucuguugn                                                19
```